(12) United States Patent
Pichichero et al.

(10) Patent No.: US 9,678,084 B2
(45) Date of Patent: Jun. 13, 2017

(54) COMPOSITIONS AND METHODS RELATED TO S100A12

(75) Inventors: Michael Pichichero, Rochester, NY (US); Kyle Liu, Rochester, NY (US)

(73) Assignee: Rochester General Hospital Research Institute, Rochester, NY (US)

(*) Notice: Subject to any disclaimer, the term of this patent is extended or adjusted under 35 U.S.C. 154(b) by 37 days.

(21) Appl. No.: 13/488,293

(22) Filed: Jun. 4, 2012

(65) Prior Publication Data
US 2013/0005836 A1 Jan. 3, 2013

Related U.S. Application Data

(60) Provisional application No. 61/493,436, filed on Jun. 4, 2011.

(51) Int. Cl.
G01N 33/68 (2006.01)

(52) U.S. Cl.
CPC ..... *G01N 33/6893* (2013.01); *G01N 2333/52* (2013.01); *G01N 2333/5428* (2013.01); *G01N 2333/70525* (2013.01); *G01N 2800/14* (2013.01); *G01N 2800/26* (2013.01)

(58) Field of Classification Search
CPC ........... G01N 33/6893; G01N 2333/52; G01N 2333/5428; G01N 2333/70525; G01N 2800/14; G01N 2800/26
See application file for complete search history.

(56) References Cited

U.S. PATENT DOCUMENTS

| | | | | |
|---|---|---|---|---|
| 6,670,136 | B2* | 12/2003 | Schmidt et al. | ............... 435/7.1 |
| 2003/0175713 | A1* | 9/2003 | Sorg et al. | ........................ 435/6 |
| 2006/0205682 | A1* | 9/2006 | Roberts et al. | ................. 514/28 |
| 2009/0258002 | A1* | 10/2009 | Barrett et al. | ............. 424/130.1 |

FOREIGN PATENT DOCUMENTS

WO 2011094535 8/2011

OTHER PUBLICATIONS

Schmidt et al., The Multiligand receptor RAGE as a progression factor amplifying immune and inflammatory responses, The Journal of Clinical Investigation, 108(7), 2001, 949-955.*
Chen, Gene expression profiles of early pneumococcal otitis media in the rate, International Journal of Pediatric Otorhinolaryngology (2005), 69, 1383-1393.*
Long et al., Differential Expression of Cytokine Genes and Inducible Nitric Oxide Synthase Induced by Opacity Phenotype Variants of *Streptococcus pneumonia* during Acute Otitis Media in the Rat, Infection and Immunity, 2003, 5531-5540.*
Sone, Expression of Intercellular Adhesion Molecule-1 in Rat Inner Ear Due to Bacterial Otitis Media, Ann Otol Rhinol Laryngol 108:1999, 648-652.*
Hirano et al., Role of Toll-like receptor 4 in innate immune responses in a mouse model of acute otitis media, Infection and Immunity, 2003, 75-83.*
Muller, Circulating biomarkers as surrogates for bloodstream infections, International Journal of Antimicrobial Agents 2007, 30S, S16-S23.*
"Prescribe." The Penguin English Dictionary. Ed. R. E. Allen. London: Penguin, 2007. Credo Reference. Web. Mar. 21, 2016, 2 pages.*
Abdelrazik, et al., "Serum level of intercellular adhesion molecule-1 in children with malignant lymphoma", Med. Princ. Pract., 17:233-8 (2008).
American Academy of Pediatrics. 2004. Subcommittee on Management of Acute Otitis Media, "Diagnosis and management of acute otitis media", Pediatrics, 113:1451-65 (2004).
Amiri, et al., "SICAM-1 as a serum marker for follow-up of pulmonary tuberculosis therapy", Tanaffos, 3:55-63 (2004).
Arola, et al., "Clinical role of respiratory virus infection in acute otitis media", Pediatr. 86:848-55 (1990).
Avadhanula, et al., "Nontypeable Haemophilus influenzae adheres to intercellular adhesion molecule 1 (ICAM-1) on respiratory epithelial cells and upregulates ICAM-1 expression", Infect. Immun., 74:830-8 (2006).
Barry, et al., "Otogenic intracranial infections in adults", Laryngoscope, 109:483-7 (1999).
Basta, et al., "Circulating soluble receptor for advanced glycation end products is inversely associated with glycemic control and S100A12 protein", J Clin Endocrinol Metab., 91:4628-34 (2006).
Baumer, et al., "Soluble intercellular adhesion molecule 1 (sICAM-1) in bronchoalveolar lavage (BAL) cell cultures and in the circulation of patients with tuberculosis, hypersensitivity pneumonitis and sarcoidosis", Eur. J. Med. Res., 3:288-94 (1998).
Bielefeldt-Ohmann, "Viral-bacterial synergistic interaction in the pathogenesis of otitis media in aboriginal children", Conf. Proceed. Medical options for prevention and treatment of otitis media in Australian Aboriginal infants, Darwin, Northern Territory, Australia, Feb. 16-18, 1992.
Biesiada, et al., "Levels of sVCAM-1 and sICAM-1 in patients with Lyme disease", Pol. Arch. Med. Wewn. 119:200-4 (2009).
Branefors-Helander, et al., "Acute otitis media. A clinical, bacteriological and serological study of children with frequent episodes of acute otitis media", Acta Otolaryngol., 80:399-409 (1975).
Broides, et al., "Cytology of middle ear fluid during acute otitis media", Ped. Infect Dis J 21(1):57-61 (2002).
Bryan, "The identification and clinical significance of large phagocyte in exudates of acute otitis media and mastoiditis", Laryngoscope, 63:559 (1953).
Budnik, et al., "Analysis of the production of soluble ICAM-1 molecules by human cells", Exp. Hematol. 24:352-9 (1996).
Buhimschi, et al., "The receptor for advanced glycation end products (RAGE) system in women with intraamniotic infection and inflammation", Am J Obstet Gynecol., 196:181 (2007).
Casey, et al., "Changes in frequency and pathogens causing acute otitis media in 1995-2003", Pediatr. Infect. Dis. J., 23:824-8 (2004).
Casey, et al., "New patterns in the otopathogens causing acute otitis media six to eight years after introduction of pneumococcal conjugate vaccine", Pediatr. Infect Dis J., 29:304-9 (2010).
Chandler, et al., "Consistency of diagnostic criteria for acute otitis media: a review of the recent literature", Clin. Pediatr., 46:99-108 (2007).

(Continued)

Primary Examiner — Andrea S Grossman
(74) Attorney, Agent, or Firm — Pabst Patent Group LLP

(57) ABSTRACT

Compositions and methods related to diagnosis of ear infections and acute otitis media.

10 Claims, 14 Drawing Sheets

(56) References Cited

OTHER PUBLICATIONS

Chihara, et al., "Soluble ICAM-1 in sputum of patients with bronchial asthma", Lancet, 343:1108 (1994).
Chini, et al., "Essential roles of NF-κB and C/EBP in the regulation of intercellular adhesion molecule-1 after respiratory syncytial virus infection of human respiratory epithelial cell cultures", J. Virol. 72:1623-6 (1998).
Cristino, "Correlation between consumption of antimicrobials in humans and development of resistance in bacteria", Int J Antimicrob Agents, 12:199-202 (1999).
El-Sawy, et al., "Soluble intercellular adhesion molecule-1 in sera of children with bronchial asthma exacerbation", Int. Arch. Allergy Immunol., 119:126-32 (1999).
Emonts, et al., "Genetic polymorphisms in immunoresponse genes TNFA, IL6, IL10, and TLR4 are associated with recurrent acute otitis media", Pediatrics, 120:814-23 (2007).
Faden, et al., "Otitis media in children: local immune response to nontypeable Haemophilusinfluenzae", Infect. Immun., 57:3555-9 (1989).
Foell, et al., "Early recruitment of phagocytes contributes to the vascular inflammation of giant cell arteritis", J Pathol., 204:311-6 (2004a),.
Foell, et al., "Expression of S100A12 (EN-RAGE) in cystic fibrosis", Thorax., 58: 613-7 (2003c).
Foell, et al., "Monitoring neutrophil activation in juvenile rheumatoid arthritis by S100A12 serum concentrations", Arthritis Rheum., 50: 1286-95 (2004b).
Foell, et al., "Neutrophil derived human S100A12 (EN-RAGE) is strongly expressed during chronic active inflammatory bowel disease", Gut.52(6):847-53 (2003a).
Foell, et al., "S100A12 (EN-RAGE) in monitoring Kawasaki disease", Lancet, 361:1270-2 (2003b).
Frick, et al., "Haemophilus influenzae stimulates ICAM-1 expression on respiratory epithelial cells", J. Immunol., 164:4185-96 (2000).
Froom, et al., "Antimicrobials for acute otitis media? A review from the International Primary Care Network", BMJ, 315:98-102 (1997).
Ganbo, et al., "Inhibition of mucociliary clearance of the eustachian tube by leukotriene C4 and D4", Ann. Otol. Rhino!. Laryngo1., 104:231-6 (1995).
Gottsch, et al., Cloning and expression of human calranulinl antigen (CO-Ag), Curr. Eye Res., 17:870-4 (1998).
Gottsch, et al., "Cloning and sequence anakysis of human and bovine corneal antigen (CO-Ag)cDNA: identification of host-parasite protein calgranulin C", Trans Am Ophthalmol Soc., 95:111-25 (1997).
Greenberg and Hoberman, "Vaccine Prevention of Acute Otitis Media", Curr Allergy Asthma Rep, 1:358-63 (2001).
Guignard, et al., "Identification and characterization of a novel human neutrophil protein related to the S100 family", Biochem J, 309:395-401 (1995).
Heikkinen, et al., "Serum interleukin-6 in bacterial and nonbacterial acute otitis media", Pediatrics, 102:296-9 (1998).
Henderson, et al., "Viral-Bacterial Synergistic Interaction in the Pathogenesis of Otitis Media in Aboriginal Children", NEJM, 306:1379-83 (1982).
Himi, et al., "Quantitative analysis of soluble cell adhesion molecules in otitis media with effusion", Acta Otolaryngol., 114:285-8 (1994).
Hitomi, et al., "A novel calcium-binding protein in amniotic fluid, CAAF1: its molecular cloning and tissue distribution", J Cell Sci., 109:805-15 (1996).
Hitomi, et al., "Novel S100 proteins in human esophageal epithelial cells: CAAF1 expression is associated with cell growth arrest", Arch Histol Cytol., 61:163-78 (1998).
Hofmann, et al., "RAGE mediates a novel proinflammatory axis: a central cell surface receptor for S100/calgranulin polypeptides", Cell, 97:889-901 (1999).

Humlicek, et al., "Modulation of airway inflammation and bacterial clearance by epithelial cell ICAM-1", Am. J. Physiol. Lung Cell. Mol. Physiol., 287:L598-L607 (2004).
Jaber, et al., "Adhesion molecule levels in serum and cerebrospinal fluid in children with bacterial meningitis and sepsis", J. Pediatr. Neurosci., 4:76-85 (2009).
Kallinich, et al., "Neutrophil-derived S100A12 as novel biomarker of inflammation in familial Mediterranean fever", Ann Rheum Dis., 69:677-82 (2010).
Kaur, et al., "Simultaneous assay for four bacterial species including Alioiococcus otitidis using multiplex-PCR in children with culture negative acute otitis media", Pediatr. Infect. Dis. J., 29(8):741-5 (2010).
Kim, et al., "The expression of RAGE and EN-RAGE in leprosy", Br J Dermatol., 154:594-601 (2006).
Klein, "Otitis media", Clin. Infect. Dis., 19:823-33 (1994).
Kosai, et al., "Elevated levels of high mobility group box chromosomal protein-1 (HMGB-1) in sera from patients with severe bacterial pneumonia coinfected with influenza virus", Scand. J. Infect. Dis., 40:338-42 (2008).
Kosaki, et al., "Increased plasma S100A12 (EN-RAGE) levels in patients with type 2 diabetes", J Clin Endocrinol Metab., 89:5423-8 (2004).
Kun, et al., "Association of the ICAM-1Kilifi mutation with protection against severe malaria in Lambarene, Gabon", Am, J. Trap. Med. Hyg., 61:776-9 (1999).
Lai, et al., "Elevated levels of soluble adhesion molecules in sera of patients with acute bronchiolitis", J. Microbiol. Immunol. Infect., 37:153-6 (2004).
Larsen, et al., "Quantification of S100A12 (EN-RAGE) in blood varies with sampling method, calcium and heparin", Scand J Immunol., 65:192-201 (2007).
Lee, et al., "Transcriptional responses of human respiratory epithelial cells to nontypeable haemophilus influenza infection analyzed by high density cDNA microarrays", J Microbiol Biotechnol., 14(4):836-43 (2004).
Leibovitz, et al., "Epidemiologic and microbiologic characteristics of culture-positive spontaneous otorrhea in children with acute otitis media", Pediatr Infect Dis J., 28(5):381-4 (2009).
Liao, et al., "Use of mass spectrometry to identify protein biomarkers of disease severity in the synovial fluid and serum of patients with rheumatoid arthritis", Arthritis Rheum 50:3792-3803 (2004).
Liu, et al., "Clinical significance of serum S100A12 in acute otitis media in young children", Pediatr Infect Dis J., 31(3):E56-8 (2012b).
Liu, et al., "Higher Serum Levels of Interleukin 10 Occur at Onset of Acute Otitis Media Caused by Streptococcus pneumoniae Compared to Haemophilus Influenzae and Moraxella Catarrhalis", Laryngoscope, 10,1002/lary,23973, [Epub ahead of print] (2013).
Liu, et al., "Serum Intercellular Adhesion Molecule 1 Variations in Young Children During Acute Otitis Media", Clin Vac Immuno, 17(12):1909-16 (2010a).
Liu, et al., "Transcriptome signature in young children with acute otitis media due to Streptococcus pneumoiniae", Microbes Infect., 14(7-8):600-9 (2012).
Marti, et al., "Host-parasite interaction in human onchocerciasis: identification and sequence analysis of a novel human calgranulin", Biochem Biophys Res Commun 221:454-8 (1998).
Matsuzawa, et al., "Association between K469E allele of intercellular adhesion molecule 1 gene and inflammatory bowel disease in a Japanese population", Gut, 52:75-8.(2003).
Melhus, et al., "Expression of cytokine genes during pneumococcal and nontypeable Haemophilus influenzae acute otitis media in the rat", Infect. Immun., 68:4024-31 (2000).
Me'Garbane, et al., "Increased diffusion of soluble adhesion molecules in meningitis, severe sepsis and systemic inflammatory response without neurological infection is associated with intrathecal shedding in cases of meningitis", Inten Care Med., 30:867-14 (2004).
Miller, et al., "Bacterial antigens and neutrophil granule proteins in middle ear effusions", Arch. Otolaryngol. Head Neck Surg., 116:335-7 (1990).

(56) References Cited

OTHER PUBLICATIONS

Murphy, "Branhamella catarrhalis: epidemiology, surface antigenic structure, and immune response", Microbiol. Rev., 60:267-79 (1996).
Naylor, et al., "Haemophilus influenzae Induces Neutrophil Necrosis A Role in Chronic Obstructive Pulmonary Disease", Am J Respir Cell Mol Biol., 37:135-43 (2007).
O\Brien, et al., "Role of alveolar epithelial cell intercellular adhesion molecule-1 in host defense against Klebsiella pneumonia", Am. J. Physiol., 276:L961-70 (1999).
Palmu, et al., "Association of clinical signs and symptoms with bacterial findings in acute otitis media", Clin Infect Dis., 38(2):234-42 (2004).
Passariello, et al., "Rhinoviruses promote internalisation of *Staphylococcus aureus* into non-fully permissive cultured pneumocytes", Microbes Infect., 8:758-66 (2006).
Petersen, et al., "Acute mastoidectomy in a Danish county from 1977-1996 with focus on the bacteriology", Int. J. Pediatr. Otorhinolaryngol., 45:21-9 (1998).
Pichichero, et al., "Antibody response to haemophilus influenza outer membrane protein D, P6, and OMP26 after nasopharyngeal colonization and acute otitis media in children", Vaccine, 28:7184-92 (2010).
Pietzsch, et al., "Human S100A12: a novel key player in inflammation", Amino Acids., 36(3):381-9 (2009).
Qvarnberg, et al., "Aspiration cytology in acute otitis media", Acta Otolaryngol., 97:443-9 (1984).
Revai, et al., "Incidence of acute otitis media and sinusitis complicating upper respiratory tract infection: the effect of age", Pediatrics., 119:e1408-12 (2007).
Rodriguez, et al., "*Streptococcus pneumoniae* causes otitis media with higher fever and more redness of tympanic membranes than Haemophilus influenzae or Moraxella catarrhalis", Pediatr Infect Dis J., 18:942-4 (1999).
Rothlein, et al., "A human intercellular adhesion molecule (ICAM-1) distinct from LFA-1", J. Immunol., 137:1270-4 (1986).
Rouleau, et al., "The calcium-binding protein S100A12 induces neutrophil adhesion, migration, and release from bone marrow in mouse at concentrations similar to those found in human inflammatory arthritis", Clin Immunol., 107:46-54 (2003).
Rudberg, "Acute otitis media: comparative therapeutic results of sulphonamide and penicillin administered in various forms", Acta Otolaryngol.,13(Suppl.):9-79 (1954).
Russo, et al., "Cell adhesion molecules and cytokines in middle ear effusions in children with or without recent acute otitis media", Otolaryngol. Head Neck Surg., 130:242-8 (2004).
Samuelson, et al., "Characterization of Haemophilus Influenzae isolates from the respiratory tract of patients with primary antibody deficiencies: evidence for persistent colonizations", Scand. J. Infect. Dis 27:303-313 (1995).
Springer, "Traffic signals for lymphocyte recirculation and leukocyte emigration: the multistep paradigm", Cell ,76:301-14 (1994).
Sulik, et al., "Increase in adhesion molecules in cerebrospinal fluid of children with mumps and mumps meningitis", Scand. J. Immunol.,64:420-4 (2006).
Teele, et al., "Otitis media in infancy and intellectual ability, school achievement, speech, and language at age 7 years. Greater Boston Otitis Media Study Group", J Infect Dis 162:685-94 (1990).
Thorton, et al., "THP-1 monocytes up-regulate intercellular adhesion molecule 1 in response to pneumolysin from *Streptococcus pneumonia*", Infect Immun, 73 (10):6493-8 (2005).
Uchiyama-Tanaka, et al., "Plasma S100A12 concentrations in peritoneal dialysis patients and subclinical chronic inflammatory disease", Ther Apher Dial., 12:28-32 (2008).
Vogl, et al., "S100A12 is expressed exclusively by granulocytes and acts independently from MRP8 and MRP14", J Biol Chem., 274:25291-6 (1999).
Witkowska, et al., "Relationship among TNF-_, sICAM-1, and selenium in presurgical patients with abdominal aortic aneurysms", Biol. Trace Element Res., 114:31-40 (2006).
Wittkowski, et al., "Acute Kawasaki disease is associated with reverse regulation of soluble receptor for advance glycation end products and its proinflammatory ligand S100A12", Arthritis Rheum., 56:4174-81 (2007).
Xie and Gu, "Moraxella catarrhalis lipooligosaccharide selectively upregulates ICAM-1 expression on human monocytes and stimulates adjacent naïve monocytes to produce TNF-alpha through cellular crosstalk", Cell. Microbiol., 10:1453-67 (2008).
Xu, et al., "Nontypeable *Streptococcus pneumonia* as an otopathogen", Diag Microbiol Inf Dis., 69:200-4 (2011).
Yang, et al., "Proinflammatory properties of the human S100 protein S100A12", J Leukocyte Biol 69:986-94 (2001).
Ye, et al., "Neutrophil-derived S100A12 is profoundly upregulated in the early stage of acute Kawasaki disease", Am J Cardiol., 94:840-4 (2004).

\* cited by examiner

Virus infection and S100A12 change
P = 0.7019, n = 3 (V+), n = 19 (V-)

Samples ns in the upper respiratory tract has increased (McCracken G H J. Emergence of resistant *Streptococcus pneumoniae*: a problem in pediatrics. Pediatr Infect Dis J 1995; 14: 424-428). The increase in antibiotic resistant pathogens provides potential hazards associated with the future treatment of bacterial infections. New diagnostic tools to distinguish AOM from normal variants of eardrum appearance during a viral upper respiratory tract infection could counteract this development, since AOM diagnosis often results in the prescription of antibiotics.

COMPOSITIONS AND METHODS RELATED TO S100A12

II. CROSS-REFERENCE TO RELATED APPLICATIONS

This application claims benefit of U.S. Provisional Application No. 61/493,436, filed Jun. 4, 2011. Application No. 61/493,436, filed Jun. 4, 2011, is hereby incorporated herein by reference in its entirety.

I. STATEMENT REGARDING FEDERALLY SPONSORED RESEARCH OR DEVELOPMENT

This invention was made with Government Support under RO1 08671 awarded by the National Institutes of Health. The Government has certain rights in the invention.

III. FIELD OF THE INVENTION

The field of the Invention relates to diagnostic methods and kits related to S100A12, IL-10, and ICAM-1 as they relate to *Streptococcus pneumonia* (Spn) and other respiratory bacterial pathogens.

IV. BACKGROUND OF THE INVENTION

Acute otitis media (AOM) is defined by the presence of middle ear effusion (MEE) with acute onset of symptoms of inflammation of the middle ear. Although more than half of patients who develop AOM have fever (Chandler, et al. 2007. Consistency of diagnostic criteria for acute otitis media: a review of the recent literature. Clin. Pediatr. (Phila.) 46:99-108), the condition is considered a localized, mucosal infection. Currently, AOM is regarded as relatively benign due to spontaneous resolution of the infection in a majority of patients (Rosenfeld, R. M., and D. Kay. 2003. Natural history of untreated otitis media. Laryngoscope 113:1645-1657.). The complications and sequelae of bacterial systemic invasion from the middle ear, including mastoiditis, brain abscess, and meningitis, are sufficiently rare that they have recently been considered less consequential in comparison to the consequences from the costs of antimicrobial treatment and overtreatment (American Academy of Pediatrics. 2004. Subcommittee on Management of Acute Otitis Media. Diagnosis and management of acute otitis media. Pediatrics 113:1451-1465).

The cause and pathogenesis of otitis media are multifactorial, involving viral and bacterial infections. The most frequently isolated bacteria in AOM are Spn (20 to 55% of cases), nontypeable *Haemophilus influenzae* (NTHi) (15 to 40%), and *Moraxella catarrhalis* (Mcat) (10 to 25%) (Casey, J. R., D. G. Adlowitz, and M. E. Pichichero. 2010. New patterns in the otopathogens causing acute otitis media six to eight years after introduction of pneumococcal conjugate vaccine. Pediatr. Infect. Dis. J. 29:304-309., Howie, V. M., R. Dillard, and B. Lawrence. 1985. In vivo sensitivity test in otitis media: efficacy of antibiotics. Pediatrics 75:8-13, Klein, J. O. 1994. Otitis media. Clin. Infect. Dis. 19:823-833). When bacteria gain entry into the middle ear space, they damage the middle ear mucosa directly by releasing toxins and indirectly by provoking both specific immunological and general inflammatory responses in the host. A prominent feature of the host response is an influx of inflammatory cells into the middle ear.

Due to difficulty in diagnosing AOM unnecessary antibiotic treatment is common which can lead to antibiotic resistant pathogens. Prevalence of antibiotic resistant pathogens in the upper respiratory tract has increased (McCracken G H J. Emergence of resistant *Streptococcus pneumoniae*: a problem in pediatrics. Pediatr Infect Dis J 1995; 14: 424-428). The increase in antibiotic resistant pathogens provides potential hazards associated with the future treatment of bacterial infections. New diagnostic tools to distinguish AOM from normal variants of eardrum appearance during a viral upper respiratory tract infection could counteract this development, since AOM diagnosis often results in the prescription of antibiotics.

Not only is an accurate diagnosis beneficial to avoid excessive and unnecessary antibiotic prescriptions, but a quick and efficient manner of determining if resolution of AOM occurs after treatment or observation, especially in children, is needed. The eardrum often does not return to its normal appearance in some patients for 6-12 weeks after infection. Concerned that AOM persists in such cases, many clinicians re-treat with even broader spectrum antibiotics when a follow up examination is not completely normal. Thus, another useful tool for AOM management would be a test that can be used to monitor individuals for the presence of infection after treatment.

The present methods, compositions, and kits provide a diagnostic tool based on specific biomarkers, such as S100A12, IL-10 and ICAM-1, samples, such as in serum, to determine whether AOM is present and caused by a bacterial infection and in follow up to determine if the infection has resolved. The biomarkers can be used in combination or alone.

V. SUMMARY OF THE INVENTION

Disclosed are methods comprising the steps of a) measuring the level of S100A12 in a subject sample; b) comparing the amount of S100A12 in the sample to a control; and c) determining whether the sample has an increased level of S100A12 compared to the control producing an S100A12 assay output, and wherein the subject has been identified as having an ear infection, a lung infection, or a sinus infection. The S100A12 can be at least 10% greater than the control.

The methods can further comprise the step of measuring the amount of IL-10 or ICAM-1 in the sample, and comparing the amount of IL-10 or ICAM-1 in the sample to a control, and determining whether the sample has an increased level of IL-10 or ICAM-1 compared to the control producing an IL-10 or ICAM-1 assay output.

In some forms, the methods include the measurement of S100A12, IL-10 and ICAM-1.

Also disclosed are the steps of obtaining the assay output, and prescribing an antibiotic for the subject in a prescription if the amount of the S100A12 is greater than the control. The methods include the step of obtaining the prescription and taking the antibiotic, or other disclosed methods can further include these steps. In some forms, the methods include the step of transmitting the assay output to a recipient.

The disclosed subjects can be a child less than 12 years of age. The disclosed samples can be a blood sample or serum sample.

The step of measuring can comprise measuring the amount of S100A12 protein or nucleic acid in the sample. Levels can be measured by performing an ELISA assay or a hybridization assay, RT, PCR, or qPCR assays.

The control can comprise a standard. The control can comprise a subject sample wherein the subject does not have an infection, as well as a subject that does not have an ear infection, lung infection, or sinus infection. Generally, the disclosed methods can be for infections such as an ear infection, lung infection, or sinus infection. The infection can be an acute otitis media infection or pneumonia.

Further disclosed are methods of diagnosing acute otitis media (AOM) in a subject comprising measuring the levels of at least two biomarkers in a sample from the subject wherein the biomarker is S100A12, IL-10 or ICAM-1, wherein increased levels of each of the measured biomarkers relative to a control means the AOM in the subject is a bacterial AOM, producing a diagnosis result.

Disclosed are methods comprising the step of obtaining the diagnosis result and prescribing an antibiotic for the subject. Also disclosed are methods, which include using the antibiotic as it was prescribed. Further disclosed are methods of obtaining the prescription and collecting the antibiotic of the prescription, placing it in a canister, and selling the antibiotic in the canister.

Further disclosed are methods of monitoring a subject having AOM that comprise treating the subject for AOM, and then performing any of the disclosed methods.

In some forms, the methods of determining that acute otitis media (AOM) is caused by *Streptococcus pneumoniae* can comprise measuring levels of one or more of the biomarkers selected from the group consisting of S100A12, IL-10 and ICAM-1, wherein increased levels of one or more biomarkers compared to levels found in other bacterial or viral infections means the individual has AOM derived from *Streptococcus pneumonia*.

In some forms, kits can comprise reagents for simultaneously assaying for a specific amount of S100A12, IL-10 and sICAM-1 on a single test strip. The kits can comprise each of S100A12, IL-10 and sICAM-1 wherein each must be present in a specific amount in order to show a positive response on the test strip.

VI. BRIEF DESCRIPTION OF THE DRAWINGS

FIG. 1 is a graph showing IL-10 and ICAM-1 serum levels in healthy vs AOM children. Serum IL-10 levels were elevated in AOM children and the change pattern was similar to that of sICAM-1. Serum IL-10 concentrations were tested by Luminex. AOM samples: from the children with AOM symptoms and signs, Spn, or NTHi or Mcat culture positive in MEF. Healthy samples: from the AOM children when they were at healthy condition. P=0.03, N=47(A), 57(H)

FIG. 2 is a graph showing IL-10 and ICAM-1 over expression in healthy vs AOM children infected with Spn. Spn induced over expression of both serum IL-10 and sICAM-1 in AOM children.

FIG. 3 is a graph of IL-10 and ICAM-1 expression in healthy vs AOM children infected with NTHi. NTHi AOM did not significantly induce over expression of either IL-10 or sICAM-1. Tope panels are of IL-10. IL-10 concentrations in AOM due to NTHi and healthy subjects. Serum IL-10 concentrations were tested by Luminex and pair-wise compared. AOM samples: from the children with AOM symptoms and signs, NTHi culture positive in MEF. Healthy samples: from the same AOM children when they were at healthy condition prior to AOM. P=0.52, N=16

Figure 6:
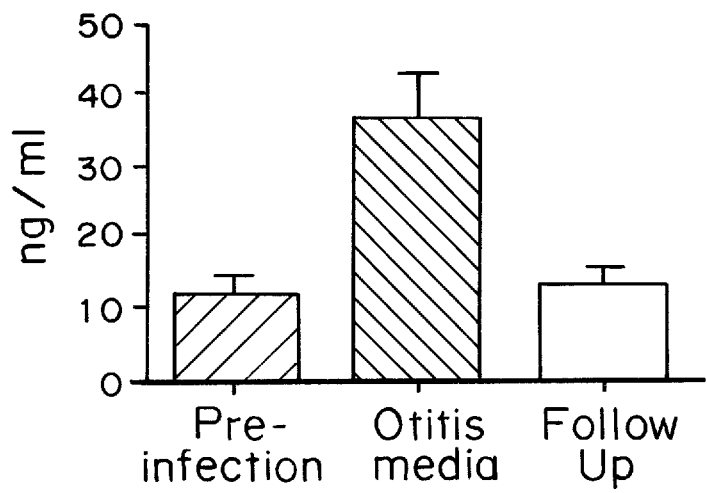

FIG. 6 is a graph of serum S100A12 levels in children with AOM. Serum S100A12 levels were elevated significantly in young children with AOM. N=69 (Pre), 116(OM), 74(F/U); OM Vs Pre, P=0.0001; OM Vs F/U, p=0.0143; Pre Vs F/U, P=0.1529.

Figure 7:
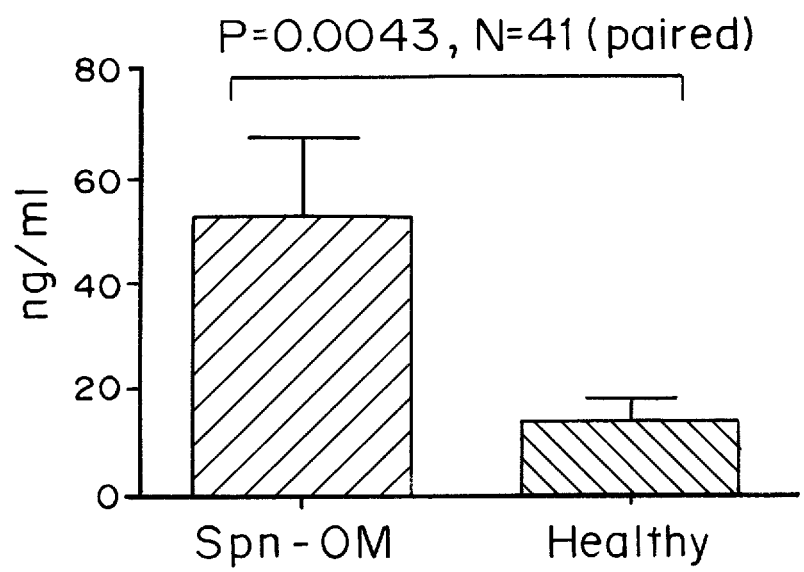

FIG. 7 is a graph of serum S100A12 levels in children with AOM infected with Spn. Serum S100A12 levels were elevated in children with AOM due to Spn.

Figure 8:
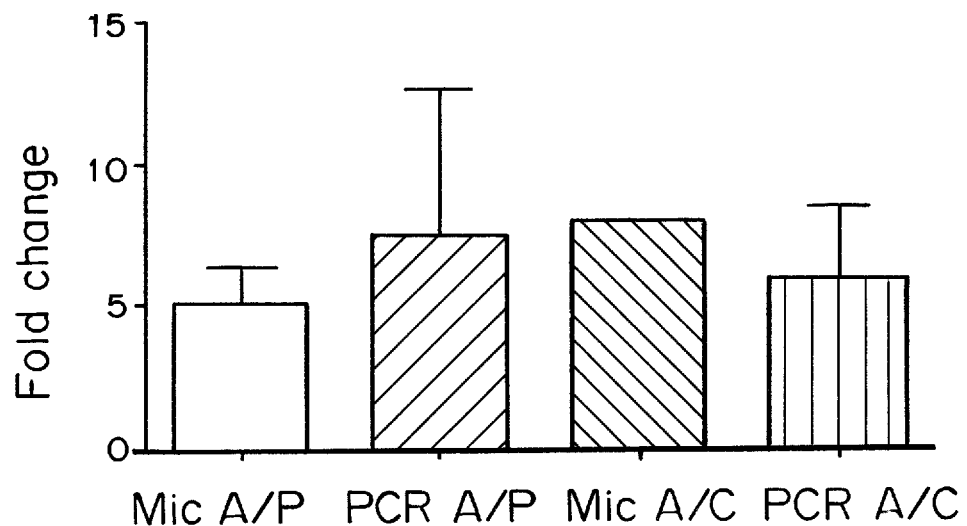

FIG. 8 is a graph of S100A12 gene expression in children with AOM infected with Spn. S100A12 gene expression was up-regulated in children with AOM due to Spn. Mc: Microarray. PCR: real time PCR (PCR). A: AOM stage P: Pre-infection healthy stage. C: convalescent stage. mRNA expression change of S100A12 in Spn-AOM children Total RNAs were extracted from PBMCs from 4 children with AOM caused by Spn, their pre-infection healthy stage or their convalescent stage, and used for microarry or real time RT-PCR analysis. The ratio of Spn-AOM (A) and pre-infection healthy stage (P) were derived from 4 different children in both microarray analysis and real time RT-PCR analysis. The ratio of Spn-AOM (A) and convalescent stage (C) were derived from 4 different children for real time RT-PCR analysis and 1 for microarray analysis.

Figure 9:
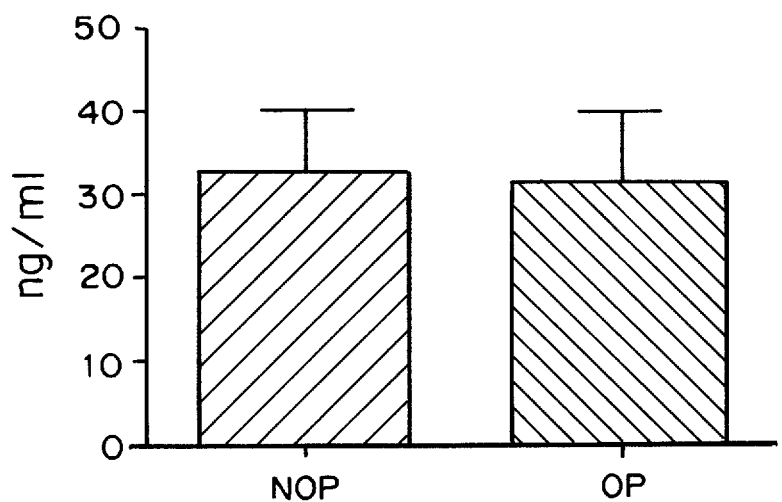

FIG. 9 is a graph of serum S100A12 levels in otitis prone vs non otitis prone children. There was no difference of serum S100A12 levels between otitis prone and non otitis prone children. p=0.2688; N=28(OP); N=84(NOP).

Figure 10:
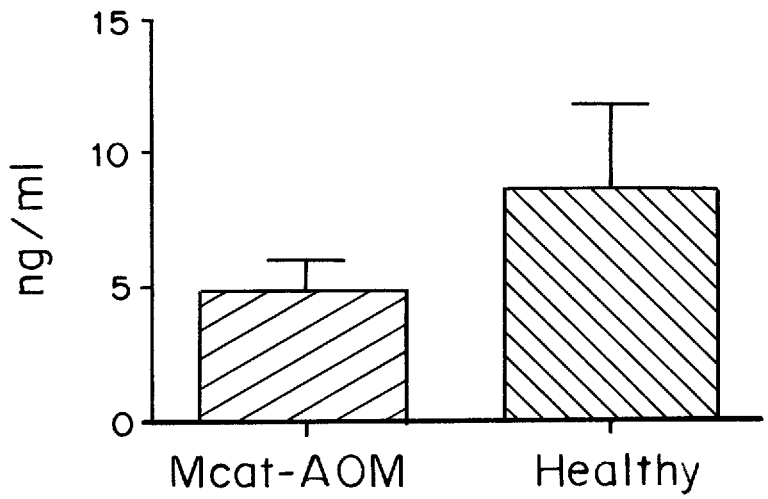

FIG. 10 is a graph of serum S100A12 in children with AOM infected with Mcat. No significant change was found for serum S100A12 in children with AOM due to Mcat.

Figure 11:
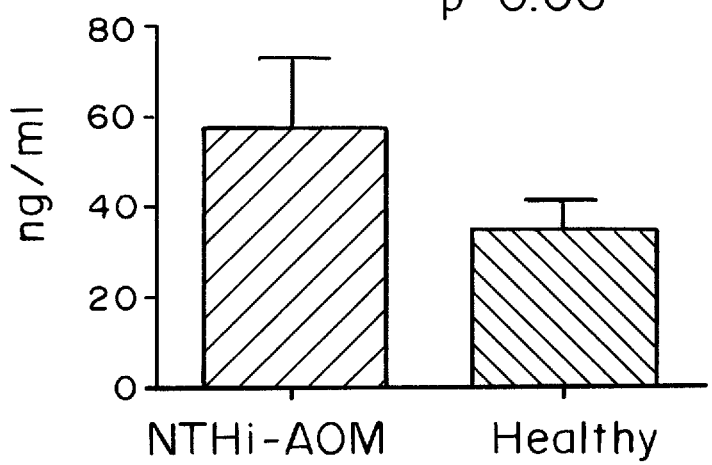

FIG. 11 is a graph of serum S100A12 levels in children with AOM infected with NTHi. No significant change was found for serum S100A12 in children with AOM due to NTHi.

Figure 12A:
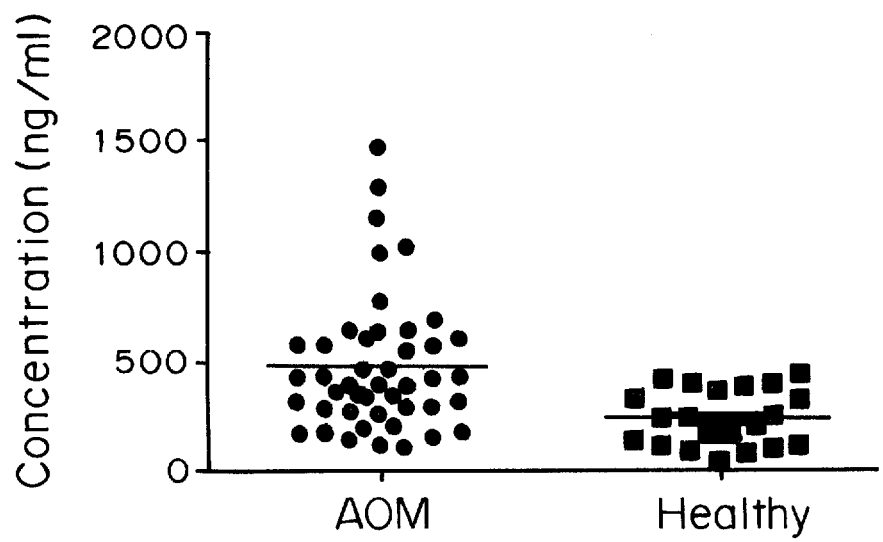
Figure 12B:
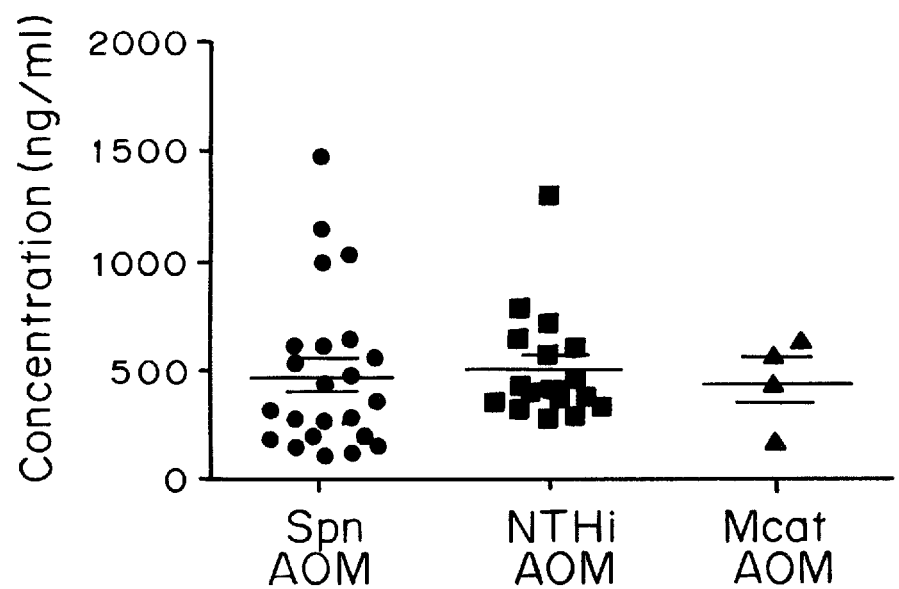

FIGS. 12A and 12B are graphs of serum ICAM-1 levels in different subject populations. (A) Comparison of serum ICAM-1 levels between 23 healthy children and 46 children with AOM. The samples were collected from the children at 6 months to 30 months of age. The middle ear fluid (MEF) of all children with AOM (n=46) was positive for otopathogens (Spn, NTHi or Mcat). Healthy children (n=23) did not have any symptoms or signs of AOM. The experiments were repeated twice, with duplicate wells being used for each test. The concentration (ng/ml) was derived from the absorbance (OD at 450 nm) based on a standard curve. (B) Comparison of the serum ICAM-1 levels among children with AOM caused by Spn, NTHi, and Mcats. The sICAM-1 levels from 46 children with AOM were analyzed (as described for panel A) with different otopathogens in the middle ears: Spn, n=24; NTHi, n=18; Mcat, n=4. No significant change existed among the groups.

Figure 13:
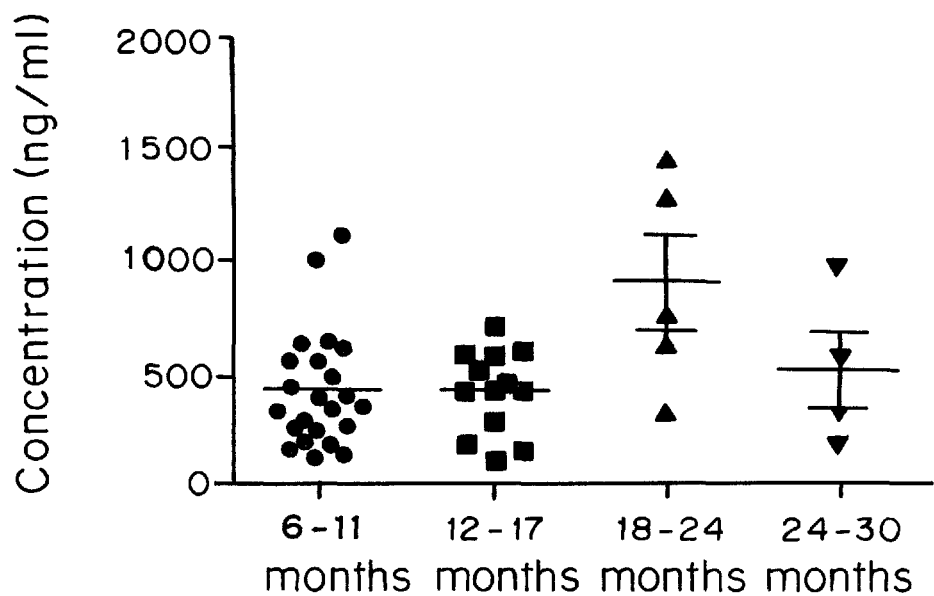

FIG. 13 is a graph of sICAM-1 level change in 46 children with AOM of different ages. P<0.05 for the group aged 18 to 24 months (M) versus the group aged 6 to 11 months (or 12 to 17 months); P>0.05 for the group aged 18 to 24 months versus the group aged 24 to 30 months.

Figure 14:
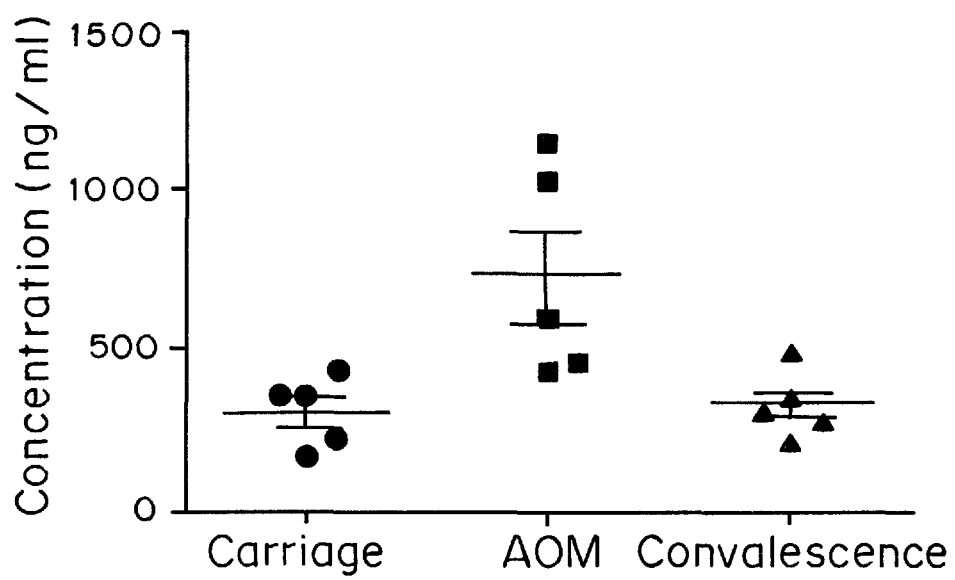

FIG. 14 is a graph of sICAM-1 levels in 5 children during asymptomatic (carriage) stage, at onset of AOM, and during convalescence from infection due to Spn, as follows: 306±134 ng/ml (mean±SD) for carriage stage, 733±323 ng/ml at onset of AOM, and 329±101 ng/ml during convalescence. P=0.02 for AOM versus carriage; P=0.03 for AOM versus convalescence.

Figure 15:
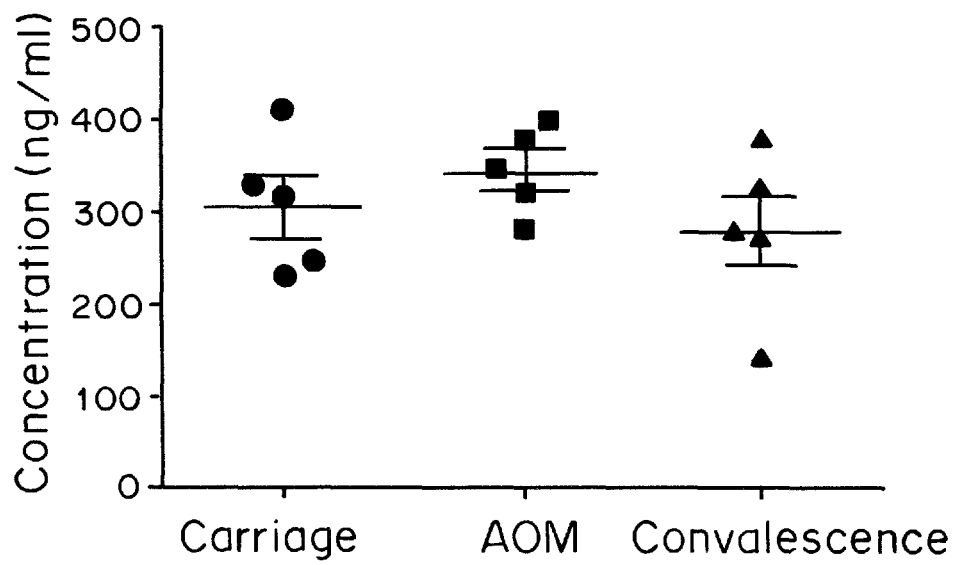

FIG. 15 is a graph of sICAM-1 levels in 5 children during asymptomatic (carriage) stage, at onset of AOM, and during convalescence from infection due to NTHi, as follows: 304±73 ng/ml (mean+/−SD) for carriage, 344±47 ng/ml at onset of AOM, and 280±87 ng/ml during convalescence. P=0.34 for AOM versus carriage; P=0.18 for AOM versus convalescence.

Figure 16:
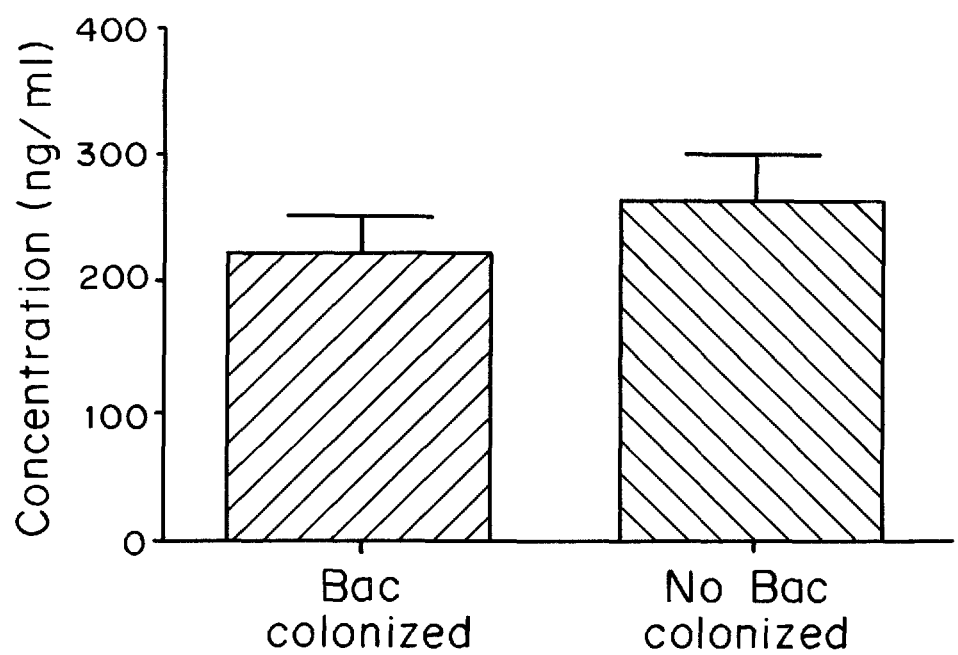

FIG. 16 is a graph comparing the sICAM-1 levels in children with otopathogen colonization (n=17) and without otopathogen colonization (n=6). The results showed that the levels of sICAM-1 were not different in the two groups (P>0.05). Bac, bacteria.

Figure 17:
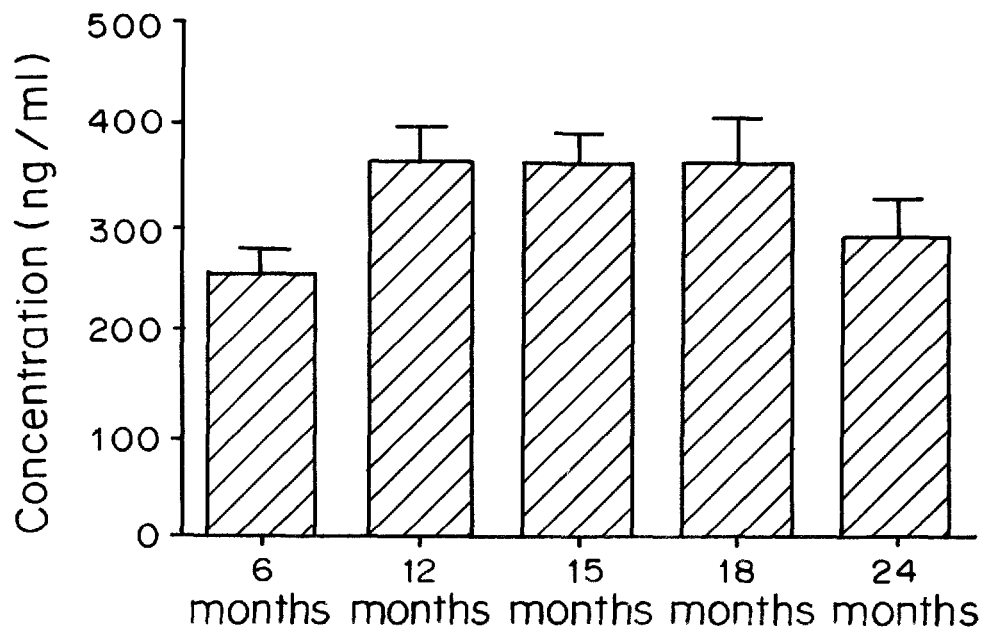

FIG. 17 is a graph comparing sICAM-1 levels in 36 healthy children without NP carriage of any AOM pathogen by age (M, months). There is no difference among the groups.

Figure 18:
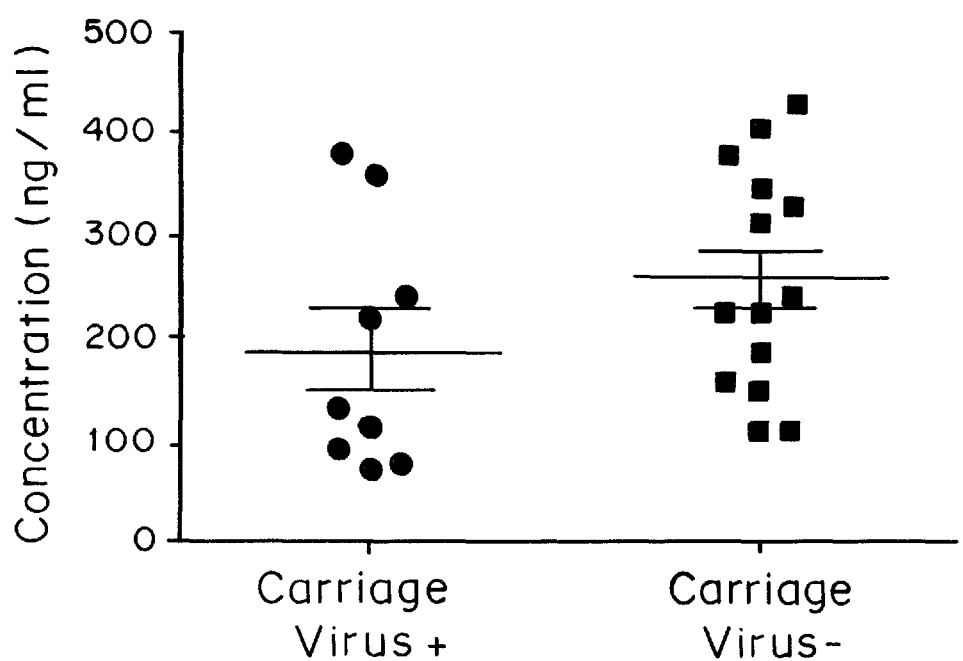

FIG. 18 is a graph of sICAM-1 levels in 9 virus-positive and 14 virus negative children when otopathogens were also present in the nasopharynx. P>0.05 for virus-positive versus virus-negative groups.

Figure 19:
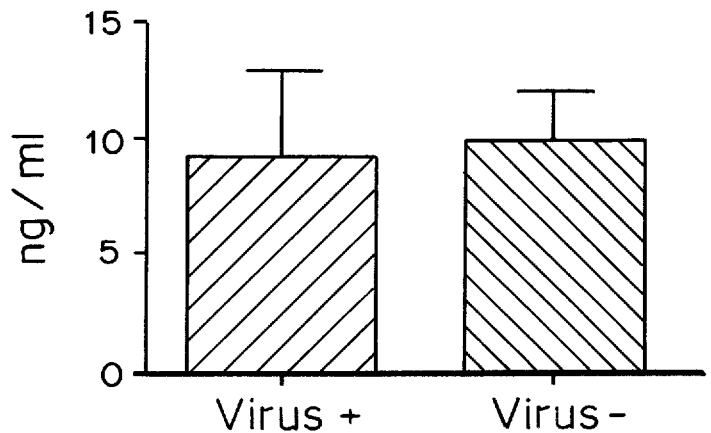

FIG. 19 is a graph showing S100A12 levels in virus infected and non-infected individuals. P=0.7019, N=3(V+), 19(V−)

Figure 20:
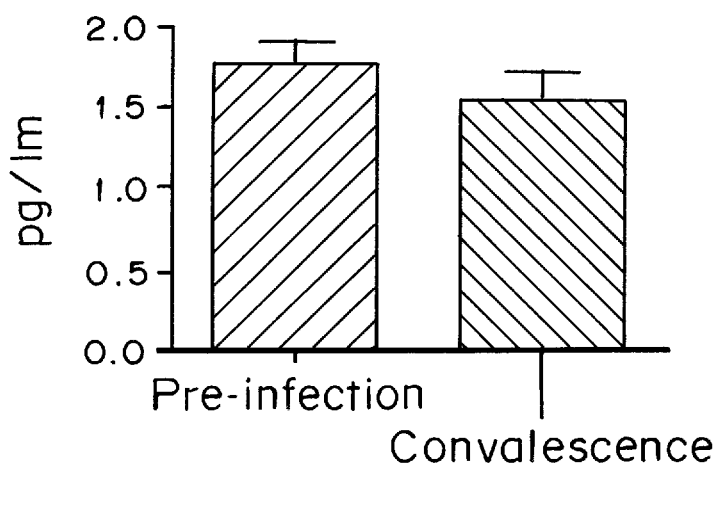

FIG. 20 is a graph showing IL-10 levels in pre-infection and convalescent stages of children with AOM due to bacterial infection. Serum IL-10 concentrations were tested by Luminex. Healthy samples: from the children prior to the onset of AOM. Convalescent samples: from the children post AOM (without AOM symptoms and signs, treated successfully. P=0.17, N=27

Figure 21:
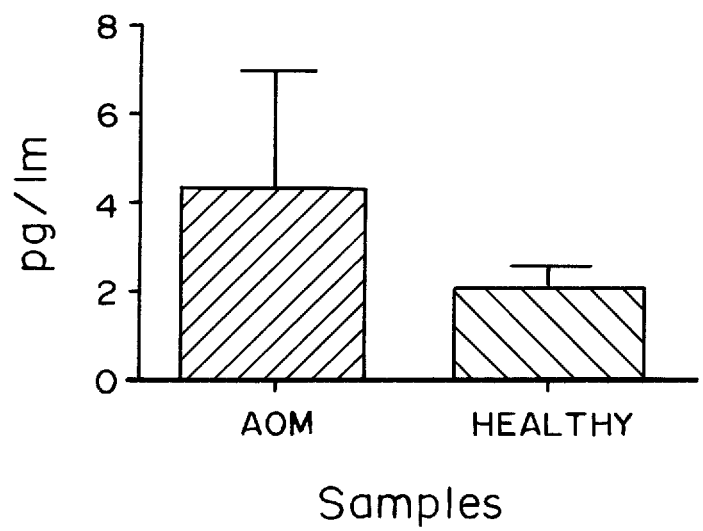

FIG. 21 is a graph showing IL-10 concentrations in AOM due to Mcat vs healthy individuals. Serum IL-10 concentrations were tested by Luminex and pair-wise compared. AOM samples: from the children with AOM symptoms and signs, Mcat culture positive in MEF. Healthy samples: from the same AOM children when they were at healthy condition prior to AOM. P=0.96, N=8

Figure 22:
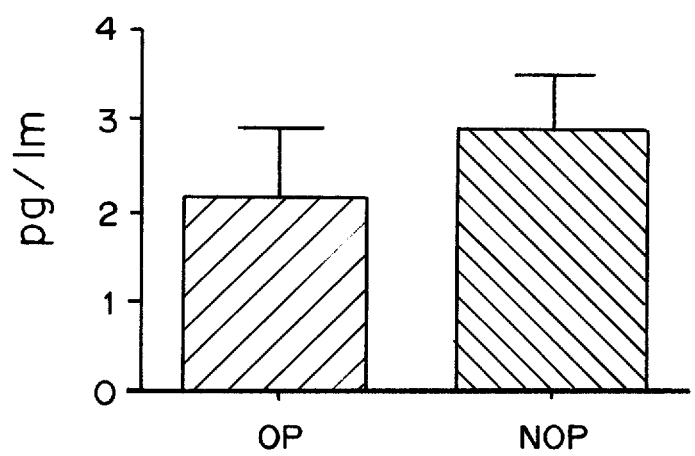

FIG. 22 is a graph comparing serum IL-10 levels between Otitis Prone (OP) and Non Otitis Prone (NOP) children.

Figure 23:
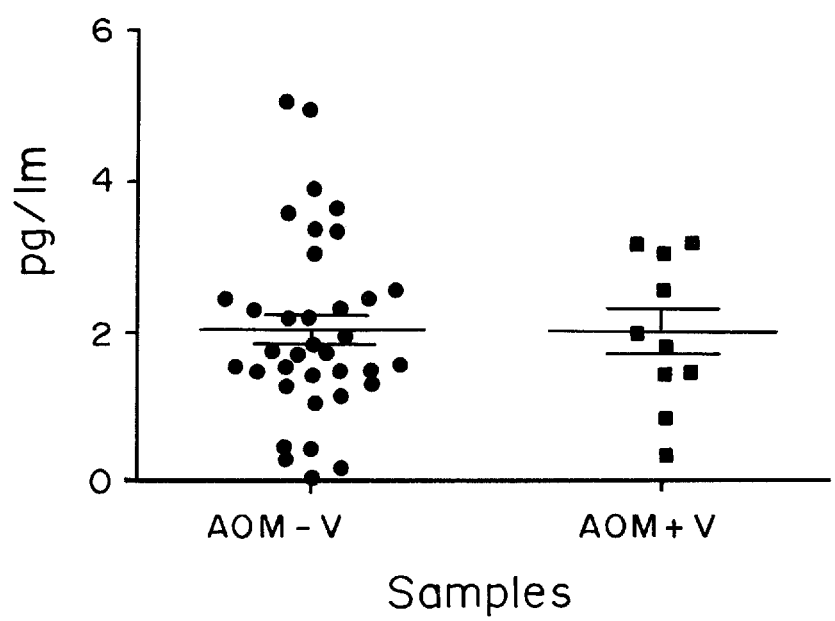

FIG. 23 is a graph comparing serum IL-10 levels in children with AOM with and without virus infection. Serum IL-10 concentrations were tested by Luminex. AOM-V samples: from the children with AOM symptoms and signs, Spn, or NTHi or Mcat culture positive in MEF, but without cold symptoms and signs. AOM+V samples: from the children with AOM symptoms and signs, Spn, or NTHi or Mcat culture positive in MEF, but with cold symptoms and signs at the same time. p=0.98, N=37(−V), 10 (+V).

VII. DETAILED DESCRIPTION OF THE INVENTION

Often when an individual gets an infection which causes inflammation, such as an ear infection or a lung infection, it is unknown as to whether the infection is a viral infection or a bacterial infection, as each can present with similar external symptoms. It is of great concern to understand whether an infection is a bacterial infection or a viral infection because the treatment courses for each would be different. In the case of a bacterial infection, the normal course of action would be to administer one or more antibiotics designed to combat the bacteria. In the case of a viral infection, often the course does not include pharmacological intervention because the antibiotics are ineffective against a virus, and viral infections typically must run their course. In extreme circumstances, heavy duty antivirals can be given. In fact, it is preferred that antibiotics not be given to patients having a mostly viral infection because the antibiotic will cause genetic selection and mutation to existing bacterial flora, such as flora that are normally not pathogenic because they are being kept in check by the immune system, but which under pressure, advantageous mutations making them more pathogenic or virulent can arise. Therefore, it is desired to be able to determine quickly and accurately whether an infection is viral or bacterial in origin so that an appropriate course of treatment can take place.

The methods, compositions, and kits disclosed herein accomplish this desire because particular immune markers are now shown to be specifically associated with bacterial infections rather than viral infections. Thus, the presence of these biomarkers in increased amounts indicates that an infection being experienced by a subject is an infection caused by a bacterium, rather than a virus. The methods are not specific for any method of detection or assay as these are well known, but rather focus on the specific markers, disclosed herein, in combination or alone, and with the infections they indicate.

Disclosed are a variety of methods each of which can include assaying samples, such as blood, tissue, or serum, from a subject, which can in turn produce an assay output, which can be used. The methods can also involve transmitting the assay output to a recipient. Typically the assays can be an in vitro assay, but under certain circumstances could be in vivo as well. Any type of assay for looking at amounts of molecules, such as hybridization assays, RT, PCR, and qPCR assays involving probes and primers, as well as ELISA assays and the like, looking at different expression of the molecules. In varying embodiments, the methods can include or utilize binding affinities and complexes, as well as a variety of components. The methods can involve contacting various reagents together, as well as using controls, such as positive controls, and they can involve normalizing as well as standards. In any embodiment disclosed, it is understood that other steps or embodiments can optionally be included or removed. In certain embodiments, the methods can utilize cells and can involve steps of comparing different results or molecules or materials or substances, or any disclosed aspect herein, by for example comparing whether they are higher, or inhibited, lower, reduced, or prevented, for example. The methods can also include the step of obtaining results or samples or the like. The methods can also include the step of determining and diagnosing, as well as looking at the confidence of a particular result or conclusion to determine its accuracy.

The methods typically revolve around bacterial infections, such as bacterial lung infections, sinus infections, and ear infections, such as pneumonias and AOMs. The methods can also include prescribing treatments, such as a prescription, such as those provided by a physician. The methods can also include treatments and treatment options, of for example antibiotics alone or in coapplication with other molecules such as pharmaceuticals or pro-drugs, having pharmacological activity. Treatments can also seek to provide a therapeutically effective amount of a drug.

In a variety of situations, ranges can be appropriate for a description of a concentration or the like.

A. Methods

1. Methods of Identifying Subjects with Bacterial Infection

The disclosed methods can comprise the steps of a) measuring the level of S100A12 in a subject sample; b) comparing the amount of S100A12 in the sample to a control; and c) determining whether the sample has an increased level of S100A12 compared to the control producing an S100A12 assay output, and wherein the subject has been identified as having an ear infection, a lung infection, or a sinus infection.

The methods can further comprise the steps of measuring the amount of IL-10 in the sample, comparing the amount of IL-10 in the sample to a control, and determining whether the sample has an increased level of IL-10 compared to the control producing an IL-10 assay output.

The methods can further comprise the steps of measuring the amount of ICAM-1 in the sample, comparing the amount of ICAM-1 in the sample to a control, and determining whether the sample has an increased level of ICAM-1 compared to the control producing an ICAM-1 assay output.

The methods disclosed herein can be performed in any combination, or alone. The biomarkers can be measured in any order, or alone as well. The methods can include measuring S100A12, then IL-10, and then ICAM-1. The methods can include measuring S100A12, then ICAM-1, and then IL-10. The methods can include measuring IL-10, then ICAM-1, and then S100A12. The methods can include measuring IL-10, then S100A12 and then ICAM-1. The methods can include measuring ICAM-1, then S100A12, and then IL-10. The methods can include measuring ICAM-1, then IL-10, and then S100A12.

In one embodiment, the methods include the step of obtaining a subject sample. For example, this step could be performed by someone other than the person or machine measuring the levels of the biomarkers. Obtaining the sample can include obtaining the sample directly from the subject or obtaining the sample from a storage area.

In certain embodiments, disclosed are methods that include the step of obtaining the assay output, and prescribing an antibiotic for the subject in a prescription if the amount of the S100A12, IL-10, ICAM-1 or any combination thereof is greater than the control. Also disclosed are methods that comprise the step of obtaining the prescription and taking the antibiotic. In addition, methods are disclosed which include filling the prescription, so obtained, for a subject.

Regardless of which biomarker or combination of biomarkers is originally measured, the methods can further comprise the step of determining the amount of the S100A12 is greater than the control.

The levels of the biomarkers in the disclosed methods can be at least 5%, 10%, 15%, 20%, 25%, 30%, 40%, 50%, 60%, 70%, 80%, 90%, 100% or greater than the control levels. In some forms the biomarker levels can be at least 1.1×, 1.5×, 2×, 2.5×, 3×, 4×, 5×, 6×, 7×, 8×, 9×, 10×, 20×, 30×, 40×, 50×, 60×, 70×, 80×, 90×, 100× or greater than the control levels. In one embodiment, the level of S100A12 levels can be at least 10% greater than the control levels.

The sample used in the disclosed methods can be a blood sample or serum sample. The sample can be any biological fluid including urine or cerebrospinal fluid.

In some forms, the methods can comprise performing an assay. The assay can be done to measure the levels of the specific biomarker of interest. The assay can include but is not limited to an ELISA, radioimmunoassay (RIA), western blot, and dot blot.

The measuring step comprises measuring the amount of biomarker mRNA in the sample. The samples can be proteins or nucleic acids. The mRNA levels of S100A12, IL-10 and ICAM-1 can all be measured. Measuring mRNA levels can comprise performing a hybridization assay or RT, PCR, or qPCR assay.

The disclosed methods can comprise a control which can be a standard. The control can comprise a subject sample wherein the subject does not have an infection. Infections of the disclosed methods can be an ear infection, lung infection, or sinus infection. The infection can be an acute otitis media infection. The lung infection can be pneumonia. The ear infection can be acute otitis media.

In some forms, the methods further comprise the step of transmitting the assay output to a recipient.

The subject of the disclosed methods can be a child less than 12 years of age. In some forms, the subject ranges in age from 1 year to 50 years old.

Further disclosed are methods wherein increased levels of S100A12, IL-10, or ICAM-1 can provide at least 50%, 60%, 70%, 80%, 90%, or 95% confidence or accuracy of the diagnosis or identification of a subject with an infection. Further disclosed are methods wherein increased levels of S100A12 and IL-10 can provide at least 80% confidence or accuracy of the diagnosis or identification of a subject with an infection. Increased levels of S100A12 and ICAM-1 can provide at least 80% confidence or accuracy of diagnosis or identification of a subject with an infection. Increased levels of S100A12, IL-10 and ICAM-1 can provide at least 90% confidence or accuracy of diagnosis or identification of a subject with an infection. The confidence or accuracy can be 50%, 60%, 70%, 80%, 90%, 95%, 98%, 99% or 100%.

2. Methods of Diagnosing

Disclosed are methods of diagnosing bacterial acute otitis media (AOM) in a subject comprising measuring the levels of at least one biomarkers in a sample from the subject wherein the biomarker is S100A12, IL-10 or ICAM-1, wherein increased levels of each of the measured biomarkers relative to a control means the AOM in the subject is a bacterial AOM, producing a diagnosis result.

The methods can further include obtaining the diagnosis result and prescribing an antibiotic for the subject. In one embodiment, the methods comprise obtaining the prescription, and using the antibiotic as it was prescribed. In one embodiment, the methods comprise obtaining the prescription and collecting the antibiotic of the prescription, placing it in a canister, and selling the antibiotic in the canister, such as filling the prescription.

3. Methods of Monitoring

The disclosed methods include methods of monitoring a subject having AOM comprising treating the subject for AOM, and then performing any of the disclosed methods.

4. Methods of Determining the Cause of AOM

Disclosed are methods of determining that acute otitis media (AOM) is caused by *Streptococcus pneumoniae* comprising measuring levels of one or more of the biomarkers selected from the group consisting of S100A12, IL-10 and ICAM-1, wherein increased levels of one or more biomarkers compared to levels found in samples from subjects having no infection, or other bacterial or viral infections means the individual has AOM derived from *Streptococcus pneumonia*.

B. Kits

The kits contain some or all of the materials needed to measure each of the 3 molecules (S100A12, sICAM-1 and IL-10) alone, in series, or simultaneously. The kit can contain a test strip that gives a positive reading only when the serum amount of each molecule exceeds a specific level. For example, for sICAM-1 the readout be positive only if the level is >400 ng/ml) since >400 has been determined to have a good sensitivity and specificity as it relates to the presence of AOM. Specific levels for S100A12 and IL-10 can be included as well. Readout of the strip would allow the clinician to have a sensitivity and specificity to consider when determining whether AOM is present or not, whether the patient has recovered in convalesence or not, and whether the AOM pathogen is Spn or not.

The kits can give one single positive reading if all three biomarkers are positive or the kits can give individual positive readings for each of the three biomarkers separately. In one embodiment, the kit can have a combination of the aforementioned. The test strip can have a spot for a positive reading for all three biomarkers together and three individual spots for positive readings of each biomarker separately.

C. Definitions

1. A, an the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Antibiotic

"Antibiotic" or like words or other forms refers to a compound, substance, molecule, or composition, which acts to reduce, inhibit, or prevent an infection of a bacteria.

3. Assaying

Assaying, assay, or like terms refers to an analysis to determine a characteristic of a substance, such as a molecule or a cell, such as for example, the presence, absence, quantity, extent, kinetics, dynamics, or binding.

4. Assay Output

An "assay output" or like terms or other forms refers to the result or product from running an assay, such as data. For example, an assay output could be the fact that S100A12 is present in a sample, after running the assay which tested whether S100A12 was present or not. The assay can be expressed in a readout on a screen, on a paper, or in any other media, such as a computer disk etc., but it must be expressed. In other words, the fact of S100A12 presence is not the assay output, it is the expression of this fact in some tangible form that is the assay output.

5. Binding Affinity

The term binding affinity as used herein can be defined as two molecules interacting with a kd of at least $10^{-3}$, $10^{-4}$, $10^{-5}$, $10^{-6}$, $10^{-7}$, $10^{-8}$, or $10^{-9}$ M or tighter binding, and can refer to for example, molecules which bind one or more of the biomarker disclosed herein, such as S100A12, IL-10, or ICAM-1 by an antibody.

6. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

7. Comprise

Throughout the description and claims of this specification, the word "comprise" and variations of the word, such as "comprising" and "comprises," means "including but not limited to," and is not intended to exclude, for example, other additives, components, integers or steps.

8. Complex

The term complex as used herein refers to the association of a first molecule with an another molecule for which the first molecule has a binding affinity.

9. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

10. Contacting

Contacting or like terms means bringing into proximity such that a molecular interaction can take place, if a molecular interaction is possible between at least two things, such as molecules, cells, markers, at least a compound or composition, or at least two compositions, or any of these with an article(s) or with a machine. For example, contacting refers to bringing at least two compositions, molecules, articles, or things into contact, i.e. such that they are in proximity to mix or touch. For example, having a solution of composition A and cultured cell B and pouring solution of composition A over cultured cell B would be bringing solution of composition A in contact with cell culture B.

It is understood that anything disclosed herein can be brought into contact with anything else. For example, a sample can be brought into contact with a reagent, such as an antibody that binds S100A12, IL-10, or ICAM-1, and so forth.

11. Coapplication

"Coapplication" is defined as the application of one or more substances simultaneously, such as in the same formulation or consecutively, within a time frame such that each substance is active during a point when the other substance or substances are active.

12. Compounds and Compositions

1. Compounds and compositions have their standard meaning in the art. It is understood that wherever, a particular designation, such as a molecule, substance, marker, cell, or reagent compositions comprising, consisting of, and consisting essentially of these designations are disclosed. Thus, where the particular designation marker is used, it is understood that also disclosed would be compositions comprising that marker, consisting of that marker, or consisting essentially of that marker. Where appropriate wherever a particular designation is made, it is understood that the compound of that designation is also disclosed. For example, if particular biological material, such as EGF, is disclosed EGF in its compound form is also disclosed.

13. Positive Control

2. A "positive control" or like terms is a control that shows that the conditions for data collection can lead to data collection.

14. Control

3. The terms control or "control levels" or "control cells" or like terms are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard. For example, a control can refer to the results from an experiment in which the subjects or objects or reagents etc are treated as in a parallel experiment except for omission of the procedure or agent or variable etc under test and which is used as a standard of comparison in judging experimental effects. Thus, the control can be used to determine the effects related to the procedure or agent or variable etc. For example, if the effect of a test molecule on a cell was in question, one could a) simply record the characteristics of the cell in the presence of the molecule, b) perform a and then also record the effects of adding a control molecule with a known activity or lack of activity, or a control composition (e.g., the assay buffer solution (the vehicle)) and then compare effects of the test molecule to the control. In certain circumstances once a control is performed the control can be used as a standard, in which the control experiment does not have to be performed again and in other circumstances the control experiment should be run in parallel each time a comparison will be made.

15. Consisting Essentially of

"Consisting essentially of" in embodiments refers to, for example, a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, decreased affinity of the cell for the biosensor surface, aberrant affinity of a stimulus for a cell surface receptor or for an intracellular receptor, anomalous or contrary cell activity in response to a ligand candidate or like stimulus, and like characteristics.

16. Comparing

"Comparing" or like words or other forms refers to the act of reviewing something in relation to something else.

17. Confidence/Accuracy of Diagnosis.

The confidence intervals can be provided as provided in the table below, as well as + or −5%, 10%, 15%, 20%, 30%, 40%, 50%, 75%, or 100% of the numbers within this table. When Table 1 was created the cutoffs, it was done by identifying the 80% level of sensitivity. From that, we determined the specificity of the test with the available data (# of samples negative by S100A12/IL-10/sICAM-1/(Total number of samples that should have been negative [pre infection or convalescent]). The values are reported next to it. Disclosed are 29. The methods and assays, wherein the determination of a bacterial infection, such as bacterial infections and methods discussed herein has at least a 50%, 60%, 70%, 80%, 90%, 95% 97%, or 99% certainty, with S100A12, ICAM-1, or IL-10 alone or in combination.

TABLE 1

| The value was cut off based on 80% AOM could generate the value greater than this | | | | |
|---|---|---|---|---|
| S100A12 | | | | |
| ng/ml | AOM (0.29-448.8 ng/ml) | Pre-infection (0.29-84.5 ng/ml) | Sensitivity | Specificity |
| >1.35 | 95 | 36 | 0.818965517 | 0.47826087 |
| <1.35 | 21 | 33 | | |
| ng/ml | AOM (0.29-448.8 ng/ml) | Convalscence (0.29-123.5 ng/ml) | Sensitivity | Specificity |
| >1.35 | 95 | 54 | 0.818965517 | 0.27027027 |
| <1.35 | 21 | 20 | | |

| ng/ml | Spn-AOM (0.29-448.8 ng/ml) | NTHi-AOM (0.29-309.1 ng/ml) | Mcat-AOM (0.78-14.9 ng/ml) | Spn Sensitivity | NTHi Sensitivity | Mcat sensitivity |
|---|---|---|---|---|---|---|
| >1.35 | 32 | 26 | 11 | 0.780487805 | 0.896551724 | 0.6875 |
| <1.35 | 9 | 3 | 5 | | | |

| IL-10 | | | | |
|---|---|---|---|---|
| pg/ml | AOM (0.08-22.5 pg/ml) | Pre-infection (0.07-4.6 pg/ml) | Sensitivity | Specificity |
| >1.3 | 38 | 43 | 0.808510638 | 0.245614035 |
| <1.3 | 9 | 14 | | |
| pg/ml | AOM (0.08-22.5 pg/ml) | Convalscence (0.06-4.6 pg/ml) | Sensitivity | Specificity |
| >1.3 | 38 | 9 | 0.808510638 | 0.653846154 |
| <1.3 | 9 | 17 | | |

TABLE 1-continued

The value was cut off based on 80% AOM could generate the value greater than this

| pg/ml | Spn-AOM (0.36-22.4 pg/ml) | NTHi-AOM (0.08-3.8 pg/ml) | Mcat-AOM (1.4-22.5 pg/ml) | Spn Sensitivity | NTHi Sensitivity | Mcat sensitivity |
|---|---|---|---|---|---|---|
| >1.3 | 14 | 10 | 8 | 0.933333333 | 0.666666667 | 1 |
| <1.3 | 1 | 5 | 0 | | | | sICAM-1

| ng/ml | AOM (110.94-1470.25 ng/ml) | Pre-infection (74.43-438.36 ng/ml) | Sensitivity | Specificity |
|---|---|---|---|---|
| >255 | 37 | 7 | 0.804347826 | 0.681818182 |
| <255 | 9 | 15 | | |

| ng/ml | AOM (110.94-1470.25 ng/ml) | Convalscence (216.08-489.38 ng/ml) | Sensitivity | Specificity |
|---|---|---|---|---|
| >255 | 37 | 14 | 0.804347826 | 0.125 |
| <255 | 9 | 2 | | |

| ng/ml | Spn-AOM (435.85-1137.21 ng/ml) | NTHi-AOM (278.19-397.69 ng/ml) | Mcat-AOM (167.02-627.94 ng/ml) | Spn Sensitivity | NTHi Sensitivity | Mcat sensitivity |
|---|---|---|---|---|---|---|
| >255 | 8 | 7 | 5 | 0.666666667 | 1 | 0.833333333 |
| <255 | 4 | 0 | 1 | | | |

18. Determining

"Determining" or like words or other forms refers to the act of settling or deciding by choice from different alternatives or possibilities.

19. Different Expression

The terms different expression and like terms can include any difference including at least a 1%, 5%, 10%, 15%, 20%, 30%, 40%, 50%, 75%, 100%, 300%, 500%, 750%, 1000%, 5000%, 10,000%, or 50,000% difference.

20. Ear Infection

Acute otitis media infection: Acute Otits Media (AOM) based on the presence of one or more of the following symptoms: fever, irritability, earache, presence of MEF (collected by tympanocentesis), inflammation and color change (red, yellow, or opaque) of the tympanic membrane, and bacterial culture positive in middle ear fluid (MEF) of patients.

21. ELISA Assay

Enzyme-linked immunosorbent assay (ELISA), also known as an enzyme immunoassay (EIA), is a form of an assay that uses biomolecules to bind to molecules to determine if they are present in a sample. Typically ELISAs are performed with antibodies and antigens but they can conceptually be performed with any molecules which bind specifically to other molecules and which can be detected. Typically, an unknown amount of antigen is affixed to a surface, and then a specific antibody is applied over the surface so that it can bind to the antigen. This antibody is linked to an enzyme, and in the final step a substance is added that the enzyme can convert to some detectable signal, most commonly a color change in a chemical substrate. As said before, this antibody can be any molecule, such as an aptamer or other peptide.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are not specifically bound. After the final wash step, the plate is developed by adding an enzymatic substrate to produce a visible signal, which indicates the quantity of antigen in the sample.

Traditional ELISA typically involves chromogenic reporters and substrates that produce some kind of observable color change to indicate the presence of antigen or analyte. Newer ELISA-like techniques utilize fluorogenic, electrochemiluminescent, and real-time PCR reporters to create quantifiable signals. These new reporters can have various advantages including higher sensitivities and multiplexing. In technical terms, newer assays of this type are not strictly ELISAs, as they are not "enzyme-linked" but are instead linked to some non-enzymatic reporter. However, given that the general principles in these assays are largely similar, they are often grouped in the same category as ELISAs.

22. Hybridization Assay

A hybridization assay or like terms is any assay that involves hybridization of a nucleic acid or other biomolecule. An immunohisto staining and FISH analysis are two examples of hybridization assays.

23. Higher

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

24. In vitro In vivo

The terms in vitro and in vivo as used herein have their usual and ordinary meanings in the art.

25. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

26. Infection

Infections of the human host are caused by bacteria, viruses, fungi and parasites. Infections elicit an inflammatory and immune response by the human host to eliminate the organism 27. Lung Infection Lung infections may be caused by bacteria, viruses, fungi and parasites and the pathological process is confined to the lower airways consisting of the trachea, bronchi, bronchioles and lung parenchyma.

28. Material Material is the tangible part of something (chemical, biochemical, biological, or mixed) that goes into the makeup of a physical object.

29. Molecule

As used herein, the terms "molecule" or like terms refers to a biological or biochemical or chemical entity that exists in the form of a chemical molecule or molecule with a definite molecular weight. A molecule or like terms is a chemical, biochemical or biological molecule, regardless of its size.

Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecule, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word "molecule" would include the specific molecule and salts thereof, such as pharmaceutically acceptable salts. It is understood that molecules can include recombinant variations or humanized variations or oligomeric or non-oligomeric variations where appropriate.

30. Normalizing

Normalizing or like terms means, adjusting data, or a response, or an assay result, for example, to remove at least one common variable.

31. Optionally

"Optional" or "optionally" means that the subsequently described event or circumstance may or may not occur, and that the description includes instances where said event or circumstance occurs and instances where it does not.

32. Obtaining

"Obtaining" or like words or other forms refers to getting or receiving or attaining. It requires to a planned effort by the actor, but the plan can be in acceptance, for example, by accepting something that is given one.

33. Pharmacological Activity

4. As used herein, the term "pharmacological activity" refers to the inherent physical properties of a peptide or polypeptide. These properties include but are not limited to half-life, solubility, and stability and other pharmacokinetic properties.

34. Pneumonia

Pneumonia is an infection of the lung parenchyma. If the infection involves the bronchi it is often termed bronchitis or bronchopneumonia.

*Streptococcus pneumonia* is a bacteria that causes ear infections, sinus infections, bronchopneumonia, pneumonia, bacteremia, septicemia, meningitis, and other bloostream-disseminated infections such as arthritis.

35. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

36. Prescribing, Prescription

"Prescribing" or "Prescription" or like words or other forms refers to a written direction or act for a therapeutic or corrective agent; specifically, such as one for the preparation and use of a medication.

37. Primers

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art, which do not interfere with the enzymatic manipulation.

38. Probes

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

39. Pro-drug

The term "pro-drug or prodrug" is intended to encompass compounds which, under physiologic conditions, are converted into therapeutically active agents. A common method for making a prodrug is to include selected moieties which are hydrolyzed under physiologic conditions to reveal the desired molecule. In other embodiments, the prodrug is converted by an enzymatic activity of the host animal.

40. Ranges

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

41. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

42. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

43. RT, PCR, qPCR

"RT, PCT, and qPCR" refer to molecular biology techniques, Reverse Transcriptase, Polymerase Chain Reaction, and quantitative PCR respectively. These techiques allow for the detection and amplification of nucleic acids from cells.

44. Sample, Blood, Serum

By sample or like terms is meant a natural product, a natural product extract, etc.; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, serum, blood, urine, stool, saliva, tears, bile) that contains cells or cell components.

45. Sinus Infection

Sinus infections are commonly termed sinusitis or rhinosinusitis. Inflammation occurs in the sinus spaces, consisting of the maxillary, ethmoid, frontal and sphenoid sinuses.

46. Subject

As used throughout, by a "subject" is meant an individual. A subject can be a patient. A subject can be preferably less than 18, 17, 16, 15, 14, 13, 12, 11, 10, 9, 8, 7, 6, 5, 4, 3, 2, or 1.

47. Standard

A "standard" or like terms or other forms refers to an established rule or measure that has been previously determined, but which can be used for comparative purposes. It often is used like a control, and often it is produced by running a control or multiple control experiments to determine a consistent or average result as a "control."

48. Substance

A substance or like terms is any physical object. A material is a substance. Molecules, cells, proteins, and DNA can be considered substances. A machine or an article would be considered to be made of substances, rather than considered a substance themselves.

49. Tissue

Tissue or like terms refers to a collection of cells. Typically a tissue is obtained from a subject.

50. Transmitting the Assay Output to a Recipient

"Transmitting the assay output to a recipient" or like terms or other forms refers to the act of sending an assay output. This can refer to for example, refer to an email from a computer, automatically generated to, for example, a doctor or doctor's office.

51. Treating

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In certain situations a treatment can inadvertantly cause harm.

52. Therapeutically Effective

The term "therapeutically effective" means that the amount of the composition used is of sufficient quantity to ameliorate one or more causes or symptoms of a disease or disorder. Such amelioration only requires a reduction or alteration or decrease, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

D. Examples

1. Example I: IL-10 Regulates Intercellular Cell-Adhesion Molecule-1 (ICAM-1) Differently in Otitis Prone Children a) Introduction ICAM-1 is typically expressed on endothelial and immune cells. When measured in the serum (sICAM-1), this molecule is a potential biomarker for AOM (Liu et al. Clin Vaccine Immunol. 2010, 17(12):1909-16), and is regulated in response to pro-inflammatory cytokines IL-10 is an important immunoregulatory cytokine produced by a variety of cells, and plays an important role in inflammatory and immune responses. It is shown herein that IL-10 level can be altered during AOM and its change can affect sICAM-1 levels.

b) Methods

Blood was collected from 6-30 month old children shortly before (healthy), during AOM, and 3 weeks later. Nontypeable *Haemophilus influenzae* (NTHi) and *Streptococcus pneumoniae* (Spn) were identified by standard culture of middle ear fluid and multiplex PCR. sICAM-1 was measured with ELISA, serum IL-10 was measured by Luminex and gene expression was tested from Peripheral Blood Mononuclear Cells by real-time RT-PCR.

c) Results

Figure 1:
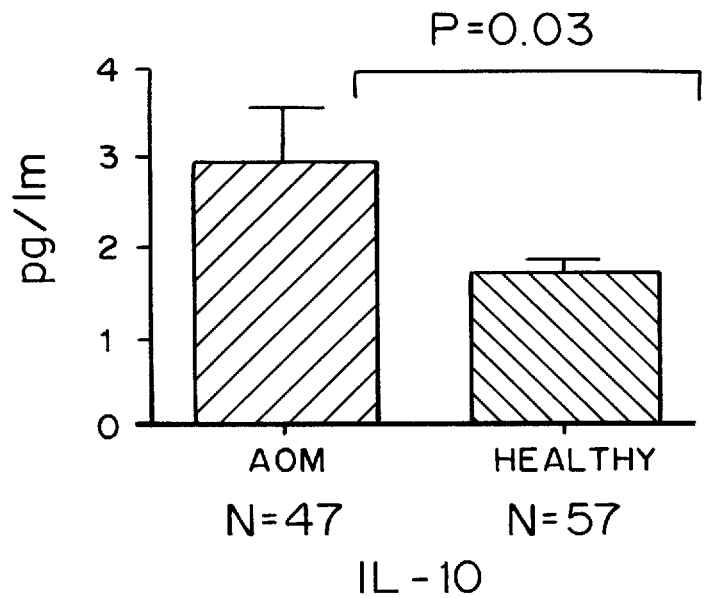
Figure 1:
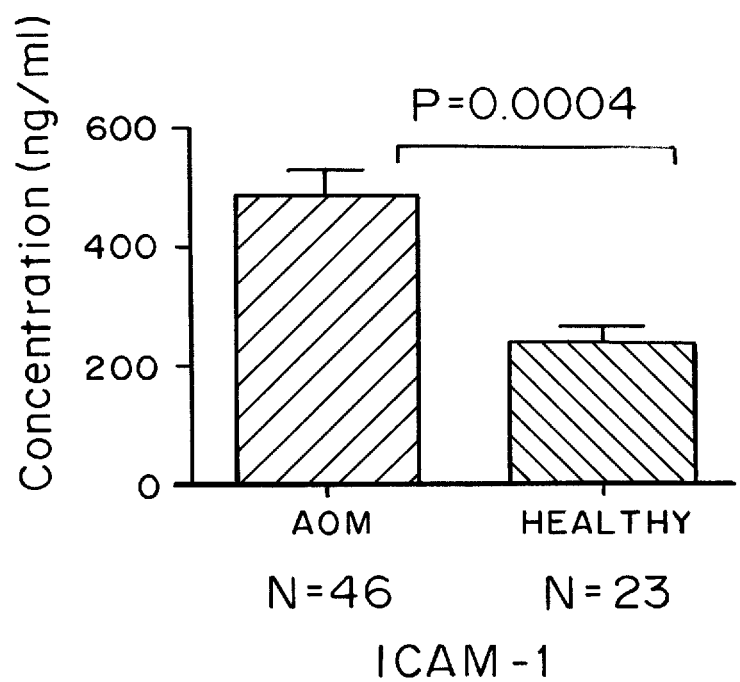

Serum concentrations of Interleukin (IL)-10 and Intercellular cell-adhesion molecule-1 (sICAM-1) were measured from young children with acute otitis media (AOM) (FIG. 1). Both of molecules showed a similar change pattern. The phenomenon was observed in RNA levels as well.

The serum concentration change of IL-10 mirrors that of sICAM-1 in otitis prone and non-prone children indicating that IL-10 is an essential modulator of AOM, functioning by regulating ICAM-1 expression.

(1) Serum IL-10 Level Change in Children with AOM:

To test if IL-10 level will be changed when children got AOM due to bacterial infection, serum IL-10 was measured from 47 children with AOM and 57 healthy children. It was found that children with AOM had a serum IL-10 level of 2.92±4.31 pg/ml while the healthy children had IL-10 levels of 1.69±0.83 pg/ml, with a significant difference (p=0.03) (FIG. 1).

(2) The Dynamic Change of IL-10 Serum Levels in Children with AOM:

Comparing IL-10 levels in 27 children from before their first incidence of AOM and after its resolution in the convalescence stage of the infection showed that there was no statistically significant difference in pre-infection group (1.95±0.85 pg/ml) and convalescent group (1.72±0.95 pg/ml) (p=0.17), which suggested that IL-10 levels could be returned to normal level after the resolution of infection (FIG. 20).

Figure 2:
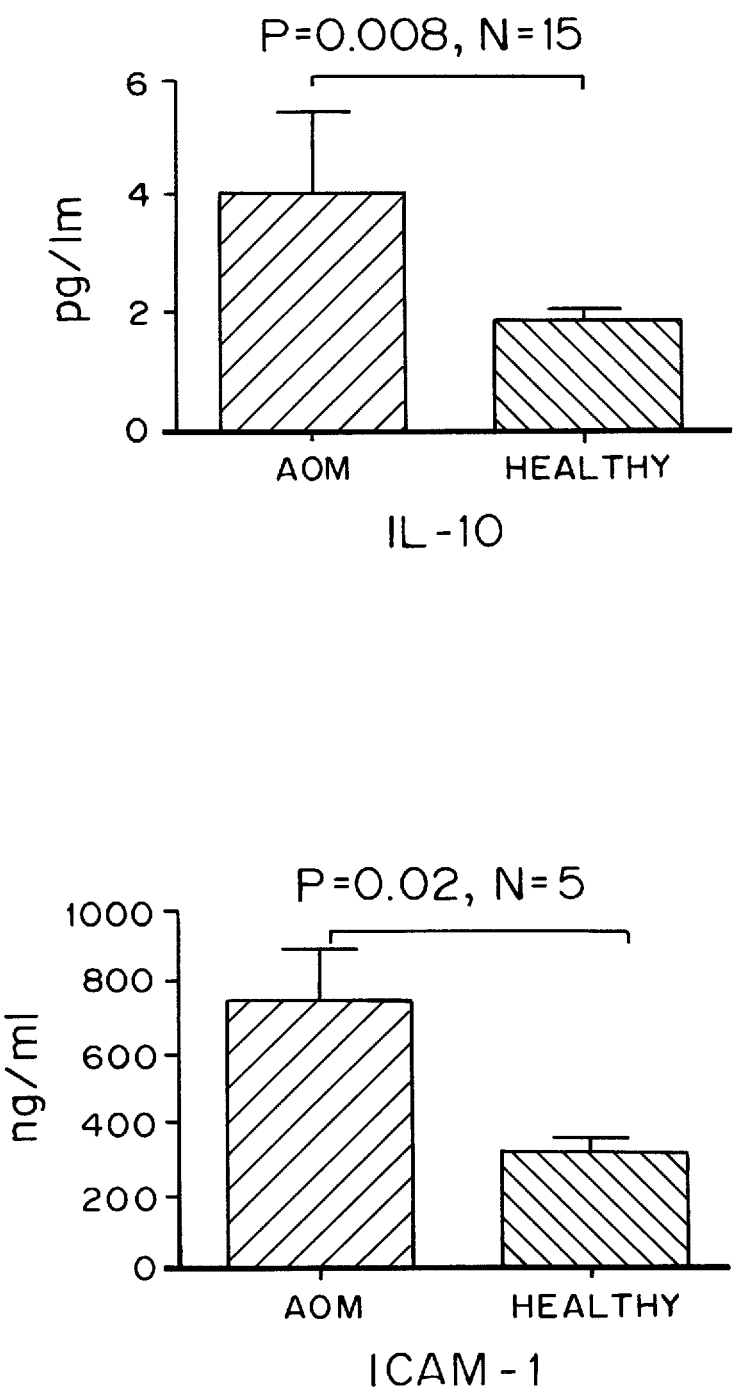

(3) Serum IL-10 Level Significantly Enhanced in Children with AOM due to *Streptococcus pneumonia*:

In 15 children who were diagnosed with AOM caused by Spn, a significant increase (3.98±5.24 pg/ml) of serum IL-10 levels was found comparing to their IL-10 levels at a healthy visit (1.82±0.83 pg/ml (p=0.008) (FIG. 2).

Figure 3:
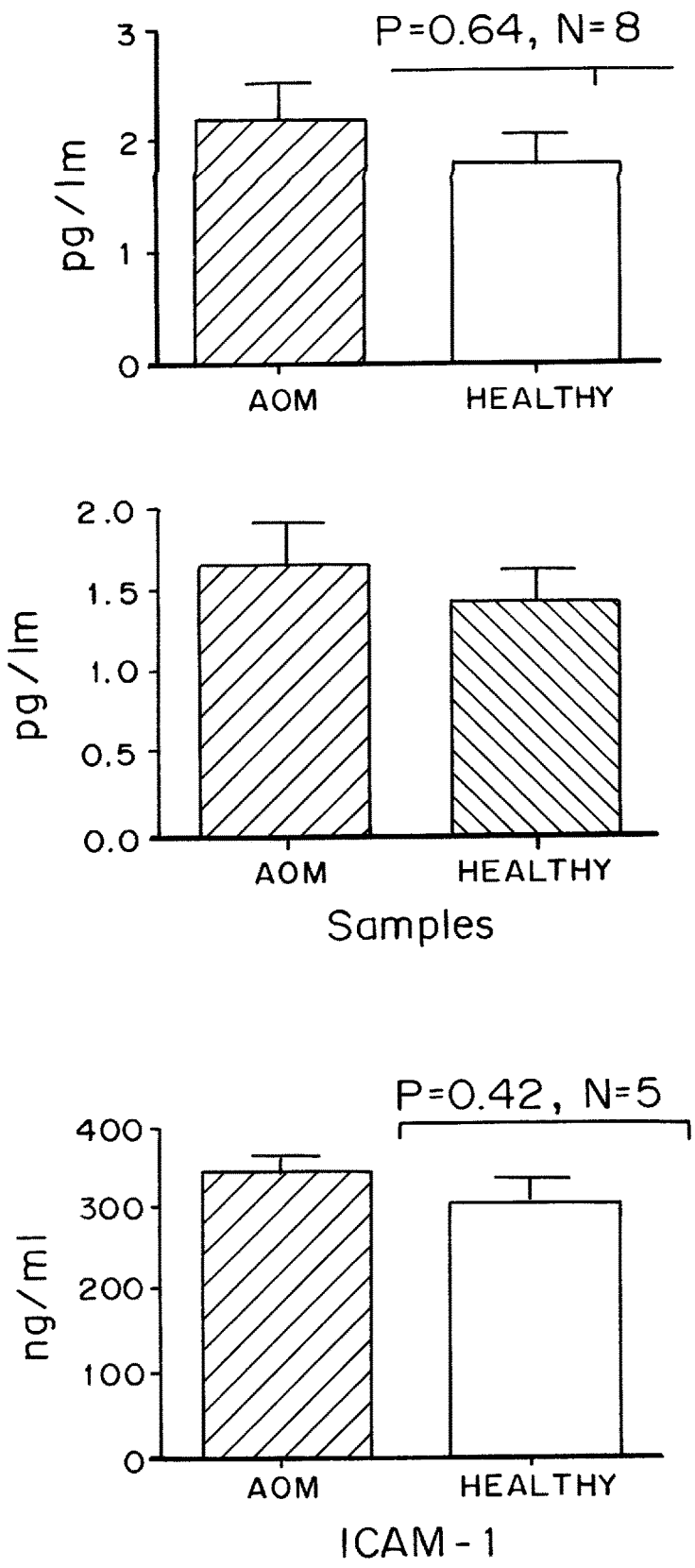
Figure 4:
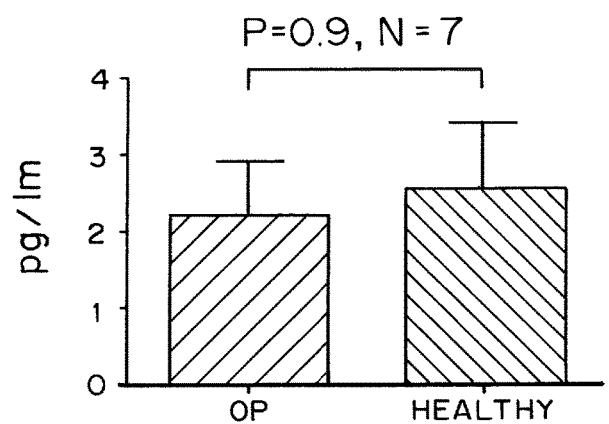
FIG. 4 is a graph of serum IL-10 concentrations in otitis prone children. Serum IL-10 concentrations did not change in otitis prone (OP) children.
Figure 5:
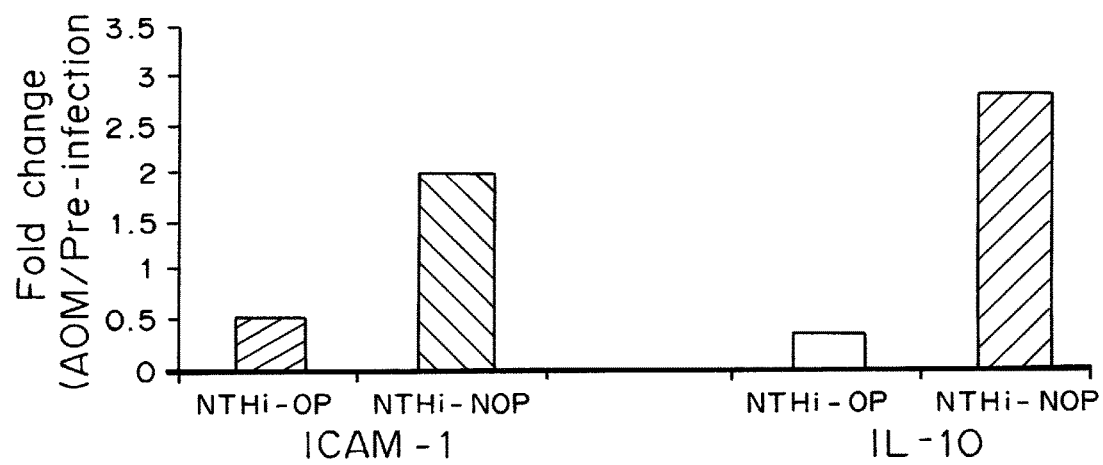
FIG. 5 is a graph of IL-10 and ICAM-1 in otitis prone children infected with NTHi. NTHi AOM did not significantly induce gene expression of either serum IL-10 or ICAM-1 in otitis prone (OP) children.

(4) Serum IL-10 Level did not Significantly Change in Children with AOM due to *Haemophilus influenza*, or *Moraxella catarrhalis*:

In the 16 children whose AOM was caused by NTHi and the 8 children whose AOM was caused by Mcat there was an increase in their serum IL-10 levels. However, it was not enough of an increase to be deemed statistically significant (p=0.52 and p=0.9 respectively) when IL-10 serum levels compared between AOM and pre-infection stages (FIGS. 3 & 21).

(5) No Significant Difference of serum IL-10 Level in Otitis Prone (OP) and Non Otitis Prone (NOP) Children:

When comparing the IL-10 serum levels in 7 otitis prone children and 47 non otitis prone children, the data showed that there was a slightly lower level of IL-10 in AOM prone children. However, the change was not statistically significant (p=0.35) (FIG. 22).

(6) Serum IL-10 Levels in Children with AOM accompanying Virus Infection:

Serum IL-10 levels were detected in 37 AOM children caused by bacteria without virus infection, and compared to the levels of IL-10 in 10 AOM children caused by bacteria but accompanying cold symptoms due to virus infection. It was found that both groups had a similar IL-10 level (p=0.98), indicating that the respiratory viruses have no statistically significant impact on the serum IL-10 level change in children with AOM (FIG. 23).

2. Example II: S100A12 is a Biomarker of Acute Otitis Media Caused by *Streptococcus pneumoniae* in Children a) Introduction S100A12 is a member of the S100 protein family, which are low molecular mass acidic proteins characterized by cell-type-specific expression and the presence of 2 EF-hand calcium-binding domains and solubility in a 100% saturated solution with ammonium sulphate. S100A12 was first described in humans by Guignard et al. in neutrophil granulocytes (Guignard et al. 1995), and later shown to be released to extracellular niches from granulocytes in response to infections, auto-immune tissue destruction, or inflammation (Bianci 2007. Foell et al. 2007a, b.) S100A12 plays important roles such as oxidant scavenging, antimicrobial activity and chemokine-like activities. Hofmann et al. (1999) identified that advanced glycation end products (RAGE) is the receptor for S100A12, so S100A12 also is called EN-RAGE (Extracellular Newly identified RAGE-binding protein). Interaction of S100A12 with cellular RAGE on endothelium, mononuclear phagocytes, and lymphocytes triggers cellular activation, with generation of key proinflammatory mediators. Extracellular S100A12 is part of the innate immune response against microorganisms (Marti et al. 1996; Gottsch et al. 1997; Gottsch and Liu 1998) and demonstrates chemotactic activity and may attract circulating and bone marrow leucocytes in inflammatory conditions (Hofmann et al. 1999; Yang et al. 2001; Rouleau et al. 2003). Elevated S100A12 serum concentrations have been found in severe bacterial infections and other acute infectious diseases (Foell et al. 2003c; Kim et al. 2006; Buhimschi et al. 2007). Increased S100A12 serum concentrations of S100A12 showed a strong correlation with granulocyte activation. However, this is the first identification of a role for S100A12 as a biomarker of acute otitis media (AOM).

AOM is a local inflammation in the middle ear and is one of the most frequent diseases of childhood. AOM is the most common reason for antibiotic treatment in childhood (Froom et al. 1997), and increasing antibiotic consumption has been shown to be related to antimicrobial resistance (Cristino, 1999). AOM episodes can impair hearing and prolonged hearing impairment in early childhood may result in long-term consequences for speech and language development (Teele et al. 1990). The direct and indirect cost of treating otitis media in children under 5 years of age in the United States was $5.0 billion in 1996 (Gates, 1996). It has been reported that neutrophils are the predominant cells involved in the early host response against AOM during invasion by bacterial pathogens, and the common pathogens identified in middle ear effusion in AOM patients are *Streptococcus pneumoniae* (Spn) (25% to 50%), nontypeable *Haemophilus influenzae* (NTHi) (15% to 30%), and/or *Moraxella catarrhalis* (Mcat) (3% to 20%), *Streptococcus pyogenes* (2% to 3%), and *Staphylococcus aureus* (2% to 3%) (Greenberg et al. 2001).

The immunologic and inflammatory transcriptome measured from peripheral blood mononuclear cells in children with AOM caused by Spn was recently described (Liu and Pichichero 2010). Therefore, in the current disclosure the expression of S100A12 was evaluated in mRNA levels and protein levels through real-time RT-PCR and ELISA from children in their healthy pre-infection stage, when they experienced AOM due to Spn, and in the convalescent stage. In addition, the pathogen specificity of the expression of S100A12 was analyzed by comparing the serum concentrations in the children with AOM caused by NTHi or Mcat as well as during upper respiratory virus infections. This study shows that the mRNA expression changes of S100A12 correlate with the development of AOM and presence specifically of Spn, indicating that S100A12 can be a useful biomarker for Spn-AOM infection and recovery.

b) Methods

Blood was Collected from 6-30 Month Old Children Prior to (healthy), at the Time of AOM and 3 Weeks After AOM. *Streptococcus pneumoniae*

(Spn), *Moraxella catarrhalis* (Mcat) and Nontypeable *Haemophilus influenzae* (NTHi) were identified by standard culture of middle ear fluid and multiplex PCR (Liu et al. Clin Vaccine Immuno. 2010, 17(12):1909-16). Serum S100A12 was measured with ELISA, and gene expression was tested from Peripheral Blood Mononuclear Cells (PBMCs) by microarray and real-time RT-PCR.

(1) Subjects

The experimental human samples were collected from the children at 6, 9, 12, 15, 18, 24, and 30 months of age. The diagnosis of AOM was based on symptoms of fever, irritability or ear ache, signs of inflammation (red or yellow color and bulging) of the tympanic membrane and the presence of middle ear fluid (MEF) as documented by tympanocentesis. After being diagnosed with AOM, children received guideline recommended antibiotic treatment and returned for a follow-up visit three weeks later. Children with a history of chronic or recurrent AOM, other infectious diseases, other local infections, or receiving steroids or other immunomodulatory agents were excluded.

(2) Preparation of Serum and Peripheral Blood Mononuclear Cells (PBMCs)

Four to 10 milliliters of heparinized peripheral venous blood from each child and control donors were drawn. The specimens were centrifuged at 2,000 rpm (Fisher Scientific Model AccuSpin-1) at room temperature (RT) for 10 min. PBMCs were isolated on Ficoll gradients and stored at liquid nitrogen, and serum was immediately stored as aliquots at −80° C. until assayed.

(3) Identification of Otopathogens

All children had tympanocentesis performed and the fluid of middle ear (0.1 to 0.2 ml) was immediately aspirated into the sterile syringe and sent for bacteriologic culture in transport medium for processing within 3 h. Identification of otopathogens from middle ear fluid was performed as described previously (Liu et al 2010).

(4) Measurement of S100A12 Protein

ELISA was performed with the CircuLex S100A12 ELISA Kit. In this assay, a monoclonal antibody specific for S100A12 has been pre-coated onto a 96-well microplate. 100 ul 1:100 diluted serum was pipetted into the wells and the immobilized antibody bound any S100A12 present. After washing away any unbound substances, an HRP conjugated polyclonal antibody specific for S100A12 was added to the wells and incubated at RT for 1 h. Following a wash to remove any unbound antibody HRP conjugate, the remaining conjugate was reacted with the substrate $H_2O_2$-tetramethylbenzidine. The absorbance of the resulting product was measured at 450 nm. A standard curve was constructed by plotting absorbance values versus S100A12 concentrations of calibrators, and concentrations of unknown samples were determined with the standard curve.

(5) Measurement of S100A12 mRNA

Total RNA was extracted from PBMCs using a QIAamp RNA blood Mini Kit (Qiagen, Maryland, USA) according to the manufacturer's instructions (Liu and Pichichero, 2010). Total RNA was reverse transcribed to cDNA using an $RT^2$ first strand kit (SABiosciences). Quantitative real-time reverse transcriptase PCR (qRT-PCR) was performed using a CFX 96 thermocycler (Bio-Rad) with $RT^2$ Profiler human custom kit.

(6) Statistical Analysis

The relative expression of genes compared with the expression in control samples in qRT-PCR data was calculated using the $\Delta\Delta C_T$ method with five housekeeping genes as controls (Liu and Pichichero, 2010). Data from ELISA were analyzed using paired and unpaired t test calculations. Comparisons between subjects and healthy controls, different otopathogen infection, and virus infection status included means and standard deviations. P values <0.05 (two-tailed) were considered statistically significant.

c) Results

Serum concentration of S100A12 was measured from young children with acute otitis media (AOM) via ELISA. The serum S100A12 level was elevated in children with AOM caused by Spn (FIG. 7) infection but not by Mcat (FIG. 10) or NTHi (FIG. 11). No difference for serum S100A12 was found between otitis prone (OP) and non otitis prone (NOP) children (FIG. 9).

Correlation of serum S100A12 to the status of AOM caused by Spn suggests that S100A12 may be a useful biomarker for distinguishing Spn-AOM from healthy children and other otopathogen caused AOM.

(1) Serum Concentration of the S100A12 Protein Increase in Children with AOM caused by Spn Infection To study the protein concentration change of S100A12 in the extracellular environment, the serum from 41 children with AOM caused by Spn infection were analyzed with ELISA. The mean age of the children was 13 months. The pre-infection, healthy stage in the same children without any AOM were used as controls. It was found that sera from patients with bacterial AOM had significantly elevated S100A12 (44.99±71.51 ng/mL) compared to controls (6.9±12.45 ng/mL. P=0.0043) (FIG. 7).

(2) Serum Concentration of the S100A12 Protein Decrease with Recovery of AOM

Usually, inflammatory mediators have short half lives and are quickly degraded in the tissue with the removal of the stimulus and resolution of inflammation (Cotran et al. 1998). To study if the serum concentration change of S100A12 reflects the presence of Spn in the middle ear and the progression of AOM, a total of 74 children were tested at a time when they were in the convalescent stage. It was found that serum levels of S100A12 at the convalescent stage dropped from the AOM stage (13.53±21.92 ng/mL), similar to the levels of the pre-infection, healthy stage (12.08±19.84 ng/mL) (FIG. 6), indicating that the S100A12 concentration change is correlated to the AOM resolution.

(3) Gene Expression of S100A12 Up-Regulated Due to Presence of Spn in the Middle Ear To verify the elevated S100A12 serum concentration is caused by gene expression change, real time RT-PCR was used to analyze the mRNA levels in 6 children when they developed AOM due to Spn infection (bacteria present in MEF and clinical AOM). It was found that the S100A12 gene was up-regulated 5 fold compared with their pre-infection healthy stage. To further evaluate the relationship between gene expression and the presence of Spn in the middle ear, the mRNA level in the convalescent stage (bacteria presumed eradicated from MEF after pathogen-directed antibiotic treatment, and without AOM symptoms and signs) was tested in the same 6 children. The results showed that the S100A12 gene expression level was decreased compared with acute Spn-AOM stage (FIG. 8), which were similar to the gene expression change status observed in microarray analysis.

(4) Serum Concentration of S100A12 Protein in AOM Caused by Other Otopathogen Infection Although Spn is a predominant pathogen identified in the middle ear in AOM children, other pathogens such as NTHi and Mcat are often found in children with AOM. To study if the serum S100A12 concentration change is pathogen-specific, 23 AOM children infected by NTHi, and 17 children infected by Mcat were selected for the serum S100A12 concentration test. It was found that the serum levels of S100A12 were not significantly enhanced in either NTHi-AOM or Mcat-AOM FIGS. 11 & 10, respectively). Serum concentration of the S100A12 protein in children during viral upper respiratory infection It is well known that AOM often follows and occurs concurrently with viral upper respiratory tract infections (Greenberg et al. 2001). To study if the presence of a respiratory virus in nasopharynx would alter the serum concentration of S100A12, we tested the serum levels of S100A12 in the sera collected from 3 children infected by parainfluenzae virus (identified by real time PCR). The comparison of the 3 samples with samples without virus infection showed no difference for S100A12 in the two groups (FIG. 19).

d) Discussion

S100A12 protein has proven to be a sensitive marker for disease activity and inflammation in bacterial infection and inflammatory disorders. The present study showed that serum concentrations of S100A12 were significantly increased in children with AOM caused specifically by Spn infection and not by AOM caused by NTHi or Mcat or by concurrent viral infection. The protein expression level correlated well with the mRNA level. This study indicates that serum S100A12 concentrations can be a useful biomarker for diagnosis of Spn-AOM and monitoring resolution after infection. It is believed that this is the first report of S100A12 expression status in children with AOM.

Constitutive gene expression of S100A12 in human tissue is almost completely restricted to neutrophil granulocytes. Although monocytes, epithelial and dendritic cells also express S100A12, the expression is quite lower than neutrophils (Guignard et al. 1995; Hitomi et al. 1996, 1998). Intracellularly, in the absence of calcium, S100A12 was found predominantly in the cytosol, whereas the addition of calcium induces translocation to membrane and cytoskeletal components, respectively (Vogl et al. 1999; Foell et al. 2004a). Engagement of the extracellular domain of membrane RAGE by S100A12 activates an intracellular signal cascades including MAP-kinase and NF-kB, induces secretion of cytokines (e.g., tumor necrosis factor- and interleukin-1b) and expression of adhesion molecules (e.g., intercellular adhesion molecule-1 and vascular cell adhesion molecule-1), and thereby mediates pro-inflammatory effects on lymphocytes, endothelial cells, neutrophils and mononuclear phagocytes (Yang et al. 2001). It is believed that the function of S100A12 is as a proinflammatory factor secreted by activated neutrophils, and S100A12 serum concentrations indicate neutrophil activation. Broides et al. found that white blood cell counts were higher in the MEF of patients with culture-positive AOM than in those with culture-negative AOM caused by *S. pneumoniae* (Broides et al. 2002). S100A12 serum concentrations have been described to be elevated in other pathological conditions such as in juvenile rheumatoid arthritis (Foell et al. 2004b), cystic fibrosis (Foell et al. 2003c), Kawasaki disease (Foell et al. 2003b), Crohn's disease (Foell et al. 2003a), and localized inflammatory processes (Pietzsch et al. 2009). Previous studies in otitis media showed that neutrophils are associated with the pathogenesis of AOM (Kamimura et al. 1995).

The current study shows that the mean serum concentration of S100A12 in normal children is 9.68±2.12 ng/mL, but the serum level of S100A12 is increased to 32.38±15.60 ng/mL when the children suffer from AOM following Spn infection. So far, normal or reference serum values of S100A12 are still debated (Larsen et al. 2007), and reference values for S100A12 in serum specimens in children have not been reported. Larsen and colleagues studied the S100A12 levels using a polyclonal ELISA and suggested that the serum S100A12 reference interval in a normal adult population, in which also persons with acute and chronic diseases are represented, should be 35-1,570 ng/mL without considering gender specific differences (Larsen et al. 2007). Normal values of healthy control subjects of selected age are expected to be lower. This seems to be consistent with data obtained by monoclonal sandwich ELISA showing mean serum S100A12 levels of healthy control subjects ranging from 10.7 to 75.0 ng/mL (Foell et al. 2003c; Kosaki et al. 2004; Ye et al. 2004; Uchiyama-Tanaka et al. 2008). However, when using other methods, like mass spectrometry, the mean levels below 10 ng/mL for healthy control subjects were obtained (Liao et al. 2004). Moreover, when comparing the reported values for healthy control subjects and several disease states, the mean serum S100A12 concentration varied more than 200-fold (Foell et al. 2003c; Kosaki et al. 2004; Basta et al. 2006; Wittkowski et al. 2007; Larsen et al. 2007; Uchiyama-Tanaka et al. 2008).

Serum levels of S100A12 were much lower in children with AOM caused by either NTHi or Mcat than AOM due to Spn. The predominance of neutrophils in the MEF during AOM was established by Bryan in 1953 (Bryan, 1953). Qvarnberg et al. (1984) found a higher number of neutrophils in AOM caused by Spn and NTHi than in AOM cases in which no pathogens were isolated. If the elevated level of S100A12 is an indication of activation of neutrophils in Spn-AOM, how can the absence of elevated levels in NTHi-AOM be explained? Broides (2002) have shown that the number of WBC counted on day 1 in the MEF of patients with AOM caused by Spn was significantly higher than the number of WBC found in the MEF of patients with AOM caused by NTHi. Naylor (2007) found when clinical isolates of NTHi were incubated in vitro with neutrophils from healthy volunteers, NTHi were phagocytosed by neutrophils but the neutrophils underwent apoptosis and released their granule contents into the extracellular environment. Those studies indicate that the role of neutrophis in NTHi is different from that in Spn. Previous clinical work has shown that AOM caused by Spn is associated with significantly more symptoms and signs of inflammation than AOM caused by NTHi or Mcat (Rodriguez and Schwartz 1999; Palmu et al 2004; Liebovitz et al 2009).

Respiratory viruses play an important role in AOM pathogenesis (Arola et al 1990; Henderson et al. 1982). Respiratory syncytial virus, rhinovirus, influenza or parainfluenza viruses was detected in two-thirds of all cases of AOM in young children. Influenza and parainfluenza viruses have neuraminidases that remove sialic acids from host-cell glycoproteins, which results in the exposure of receptors for pneumococci, thereby promoting attachment of Spn to nasopharyngeal epithelial cells. To verify if the serum levels of S100A12 in AOM children were affected not by concurrent virus infection, the difference of serum levels of S100A12 was evaluated between respiratory virus positive children and the healthy, virus negative children. As expected no differences were found because activated neutrophils are known to secrete S100A12, and many viral diseases, including parainfluenza, influenza, rubella, rubeola, and mumps decrease the neutrophil count. (Abramson et al. 1982, Abramson et al. 1994, Vega, 2009)).

The current disclosure indicates that the serum concentration of S100A12 can be a valuable biomarker for diagnosis and recovery from AOM caused by Spn.

3. Example III: Serum Intercellular Adhesion Molecule 1 Variations in Young Children with Acute Otitis Media a) Introduction The migration of leukocytes into sites of inflammation is mediated by numerous factors, including intercellular adhesion molecule 1 (ICAM-1; CD54). ICAM-1 is a member of the immunoglobulin (Ig)-like superfamily (Rothlein et al. 1986. A human intercellular adhesion molecule (ICAM-1) distinct from LFA-1. J. Immunol. 137:1270-1274); it is expressed on endothelial cells, monocytes, fibroblasts, leukocytes, epithelial cells, macrophages, mitogen-stimulated T lymphoblasts, germinal center B cells, and dendritic cells (Sulik et al. 2006. Increase in adhesion molecules in cerebrospinal fluid of children with mumps and mumps meningitis. Scand. J. Immunol. 64:420-424). Soluble isoforms of ICAM-1 (sICAM-1) shed from the surface of activated cells and can be quantified in biological fluids, allowing insights into early events of leukocyte recruitment (Springer, T. A. 1994. Traffic signals for lymphocyte recirculation and leukocyte emigration: the multistep paradigm. Cell 76:301-314). sICAM-1 levels have been reported to be the initial marker of inflammatory reactions in various diseases, such as allergic rhinitis, tuberculosis, sarcoidosis, rheumatoid arthritis, and meningitis (Amiri et al. 2004. SICAM-1 as a serum marker for follow-up of pulmonary tuberculosis therapy. Tanaffos 3:55-63, Baumer et al. 1998. Soluble intercellular adhesion molecule 1 (sICAM-1) in bronchoalveolar lavage (BAL) cell cultures and in the circulation of patients with tuberculosis, hypersensitivity pneumonitis and sarcoidosis. Eur. J. Med. Res. 3:288-294, Jaber et al. 2009. Adhesion molecule levels in serum and cerebrospinal fluid in children with bacterial meningitis and sepsis. J. Pediatr. Neurosci. 4:76-85, Me'garbane et al. 2004. Increased diffusion of soluble adhesion molecules in meningitis, severe sepsis and systemic inflammatory response without neurological infection is associated with intrathecal shedding in cases of meningitis. Intensive Care Med. 30:867-874). However, to date, there is no information on sICAM-1 expression in children with AOM.

In this study, the first to ever evaluate the concentrations of systemic (serum) sICAM-1 from children with AOM, it was determined if (i) the levels of sICAM-1 increased during *S. pneumoniae*, nontypeable *H. influenzae*, or *M. catarrhalis* infections; (ii) sICAM-1 levels, as a marker of the innate immune response, varied among children with AOM; (iii) sICAM-1 levels increased when children developed AOM compared to their sICAM-1 levels before infection; and (iv) the sICAM-1 level returned to the pre-AOM level at the convalescent stage of AOM after successful antimicrobial therapy.

b) Methods (1) Subjects

The experimental human samples evaluated in this study were collected in the first 3 years to 5 years as part of a prospective study funded by the National Institute for Deafness and Communication Disorders that commenced in June 2006. All the samples were collected from the children at 6, 9, 12, 15, 18, 24, and 30 months of age. Informed consent was obtained at enrollment from the parents or guardians.

The diagnosis of AOM was based on symptoms of fever, irritability, or earache; signs of inflammation (red or yellow color or bulging) of the tympanic membrane; and the presence of middle year fluid (MEF), as documented by tympanocentesis. After being diagnosed with AOM, patients received various antibiotic treatments and returned for a follow-up visit 3 weeks later, in addition to scheduled visits. Children with a history of chronic or recurrent AOM, other infections, chronic diseases, and other diseases were excluded. A virus infection was diagnosed on the basis of the observation and examination of clinical symptoms and signs, such as fever, rhinorrhea, and cough, along with a decreased white blood cell count and a predominance of lymphocytes, and verified via multiplex PCR using a Seeplex RV12 detection kit (Seegene, M D), following the manufacturer's instruction.

(2) Serum and PBMCs

Blood specimens were collected from the study patients at each visit. Four milliliters of heparinized peripheral venous blood was drawn from each patient and control donor. The specimens were centrifuged at 2,000 rpm (model AccuSpin-1; Fisher Scientific) at room temperature for 10 min. Peripheral blood mononuclear cells (PBMCs) were isolated on Ficoll gradients and stored at −80° C. Serum was immediately stored as aliquots at −80° C. until it was assayed.

(3) MEF

Tympanocentesis was performed for all patients with the use of a 20-gauge spinal needle attached to a 3.0-ml sterile syringe; the anteroinferior portion of the intact tympanic membrane was punctured. The fluid (0.1 to 0.2 ml) was immediately aspirated into the sterile syringe and sent in transport medium for processing for bacteriologic culture within 3 h.

(4) Bacteriology

Swabs of the middle ear aspirate were plated on Trypticase agar medium containing 5% sheep blood and chocolate agar. The plates were incubated aerobically at 37° C. in a 5% CO2 atmosphere for 48 h. Presumptive identification of *S. pneumoniae* was based on the presence of alpha hemolysis and inhibition of optochin, and the identity was confirmed by a positive slide agglutination test, according to established CLSI procedures.

Identification of *Haemophilus influenzae* was based on Gram's stain, growth on chocolate agar medium, failure to grow on Trypticase agar with added sheep blood, and a nutritional requirement for both hemin and NAD. Organisms that failed to agglutinate with polyvalent antisera to *H. influenzae* groups a, c to f, and b (Phadebact; Pharmacia) were considered untypeable. Identification of *M. catarrhalis* was based on Gram's stain, oxidase reaction, and the catarrhalis disk reaction (Remel, K S). Whenever the pathogen was questionable, verification of the identity of the pathogen was performed by multiplex PCR, as described previously (Kaur et al. 2010).

(5) sICAM-1 Assay sICAM-1 levels in the serum samples were measured using specific sandwich immunoassays (enzyme-linked immunosorbent assay [ELISA] kits from Bender MedSystems Europe, Vienna, Austria) based on recombinant soluble adhesion molecules supplied by the manufacturer's standards. Ninety-six-well ELISA plates were coated with capture anti-human sICAM-1 monoclonal antibody (MAb). All serum samples were diluted in diluent buffer provided with the kits. The known standards and duplicate test samples were added, and the mixtures were incubated for 2 h at room temperature. After the binding of sICAM-1 to the immobilized MAb, a second peroxidase (horseradish peroxidase)- conjugated streptavidin detecting anti-human sICAM-1 monoclonal antibody was added for 1 h. For color development, substrate solution [2,2'-azinobis(3-ethylbenzthiazolinesulfonic acid)] with 0.03% H2O2 was added. The optical densities (ODs) of the plates at 450 nm were read with a microplate reader. Standard curves were generated using known concentrations of human sICAM-1in a series of dilutions ranging from 10 ng/ml to 0.156 ng/ml. Because the concentration in each sample corresponds to the OD readout of the sample, its value was derived from standard curves by regression analysis. Final concentrations were calculated by multiplying the given values by the dilution factor, the results are reported as the mean concentration (ng/ml) ±standard deviation (SD). Each experiment was repeated at least twice.

(6) Microarray

Total RNA was extracted from PBMCs using a QIAamp RNA blood minikit (Qiagen, MD), according to the manufacturer's instructions. Double-stranded cDNA generated from total RNA was labeled with cyanine 5 and subsequently hybridized to 30,968 human genome probes and 1,082 experimental control probes in a Human OneArray array system, according to the manufacturer's standard protocols (PhalanxBio Inc., CA). Microarrays were scanned at 5-µm resolution using an Agilent scanner. Raw intensity signals for each microarray were captured using a Molecular Dynamics Axon 4100A scanner and were measured using GenePixPro software. The data from all microarrays in each experimental set were then analyzed using Omicsoft Array Studio software; control and missing features were removed, and the remaining signals were quantile normalized. Student's t test was performed after technical replicates were combined to calculate P values.

(7) qRT-PCR

One hundred nanograms of total RNA was reverse transcribed to cDNA using an
RT2 first-strand kit (SABiosciences, MD). Quantitative real-time reverse transcriptase PCR (qRT-PCR) was performed using an RT2 profiler PCR array system kit (SABiosciences) with a CFX 96 thermocycler (Bio-Rad). The threshold and baseline were set automatically using the PCR/array analysis method, according to the manufacturer's instructions (SABiosciences). Threshold cycle (CT) data were uploaded into the data analysis template on the manufacturer's website (SABiosciences). The relative expression of genes compared with the expression in control samples was calculated on the website using the ΔΔCT method and five housekeeping genes as controls.

(8) Statistical Analysis

Analysis of variance was used for analyzing multiple-group data. Two-tailed analysis was used throughout, with significance defined as a P value of <0.05. Power analysis was done using paired and unpaired t test calculations. The statistical analysis included both paired analysis for each patient (AOM at the acute-phase visit versus AOM at the convalescent-phase visit) and comparison of the magnitude of the changes in the mean values. Comparisons between patients and healthy controls included means and standard deviations.

c) Results (1) Serum Levels of sICAM-1 in Children with AOM

A total of 46 children with AOM, including 23 males and 23 females, were analyzed. The mean age of the children was 13 months. The children were infected with S. pneumoniae (n=24), nontypeable H. influenzae (n=18), or M. catarrhalis (n=4). Twenty-three age-matched healthy children without any AOM symptoms or signs were used as controls for comparison. It was found that sera from patients with bacterial AOM had significantly elevated sICAM-1 levels (479±305 ng/ml) compared to those for the controls (232±117 ng/ml) (P=0.0004) (FIG. 12A). There was no significant difference in serum sICAM-1 levels among children infected by S. pneumoniae, nontypeable H. influenzae, or M. catarrhalis (FIG. 12B).

(2) sICAM-1 Levels vary Among Children with AOM

The systemic adaptive immune response to AOM is known to vary among children by age at the time of infection, a key predictor of the response to treatment. Therefore, the variations in sICAM-1 levels were evaluated among the 46 children with AOM described above according to the age of the child at the time of infection (FIG. 13). It was found that there were no changes in sICAM-1 levels among children who experienced AOM at age 18 months. However, the levels of sICAM-1 were significantly increased when the children experienced AOM at the age of 18 to 24 months compared to the levels in younger children (P<0.05). For 24- to 30-month-old children with AOM, the levels of sICAM-1 were not statistically different from those in the younger group of 6 to 18 months of age, but only 4 children were in the oldest age group.

(3) Serum sICAM-1 Dynamic Change During AOM Progression

AOM development occurs as a dynamic progression, including the asymptomatic carriage, AOM, and convalescent stages. To study the status of serum sICAM-1 during the progression of AOM, a total of 10 children at a time were tested when they were experiencing asymptomatic carriage of an ototpathogen (during the healthy stage without AOM symptoms and signs), when the children developed AOM (when bacteria were present in MEF and clinical AOM), and in the convalescent stage (when bacteria were presumed to be eradicated from MEF after pathogen-directed antibiotic treatment). It was found that the patterns of change in sICAM-1 levels were different for S. pneumoniae and nontypeable H. influenzae. For 5 children studied who developed AOM due to S. pneumoniae, it was found that serum levels of sICAM-1 were low (306±134 ng/ml) when children were in the healthy stage and S. pneumoniae was carried in the nasopharynx (NP), that ICAM-1 levels significantly increased (733±323 ng/ml) when the children experienced AOM compared to the levels during their carriage stage (P<0.05), and that sICAM-1 levels dropped back to the levels of the asymptomatic carriage stage after successful antibiotic treatment (FIG. 14). The serum sICAM-1 levels for 5 children who carried nontypeable H. influenzae in their NPs, then developed AOM from nontypeable H. influenzae, and then recovered after antibiotic therapy are shown in FIG. 15. The pattern of sICAM-1 levels for children infected with H. influenzae appears to be different from that for children infected with S. pneumoniae. Asymptomatic carriage in the NPs was associated with a modest elevation in the level of sICAM-1 (304±73 ng/ml); increased during AOM, but not significantly (P=0.34); and fell toward normal during convalescence.

(4) Serum Levels of sICAM-1 in Healthy Children with and without Nasopharyngeal Carriage of Otopathogens The bacterial carriage of otopathogens in the NPs of healthy children is quite common (20 to 50%), and carriage rates are 100% during AOM episodes (Faden et al. 1989. Otitis media in children: local immune response to nontypeable Haemophilus influenzae. Infect. Immun. 57:3555-3559, Samuelson et al. 1995. Characterization of Haemophilus influenzae isolates from the respiratory tract of patients with primary antibody deficiencies: evidence for persistent colonizations. Scand. J. Infect. Dis. 27:303-313). To investigate whether or not NP colonization by otopathogens in healthy children influences the expression of sICAM-1, sera were collected from 17 healthy children with bacterial colonization of the NPs and 6 children without bacterial colonization of the NPs. No significant difference in the levels of sICAM-1 in the NPs of children colonized with otopathogens (222±124 ng/ml) and children not colonized with bacteria (262±97 ng/ml) was found (FIG. 16).

(5) Serum Levels of sICAM-1 in Healthy Children of Various Ages

The sICAM-1 levels in 36 additional children were also evaluated when they were healthy at different ages. The tests were performed when children were 6 months (n=20), 12 months (n=3), 15 months (n=4), 18 months (n=4), and 24 months (n=5) old. Serum sICAM-1 levels in 6-month-olds were lower than those in the other groups, but the difference was not statistically significant (FIG. 17).

(6) Serum Levels of sICAM-1 during Viral URI and Nasopharyngeal Carriage of Otopathogens It is known that AOM occurs concurrently with viral upper respiratory tract infections in >90% of cases of AOM in children (Revai et al. 2007. Incidence of acute otitis media and sinusitis complicating upper respiratory tract infection: the effect of age. Pediatrics 119:e1408-e1412). Viral upper respiratory infection (URI) impairs host defenses, thereby contributing to subsequent bacterial superinfection. To study if the presence of a respiratory virus in the NPs would change the expression of sICAM-1, the sera from the 9 children clinically diagnosed to be infected by a respiratory virus and 14 children without an apparent respiratory virus infection were tested; no difference in sICAM-1 levels was found (FIG. 18). Among the 9 samples from children with clinically diagnosed virus infection, 2 samples with medium serum sICAM-1 levels were selected to check the virus species by multiplex PCR, and it was found that both of the samples were parainfluenza virus positive.

(7) Transcription Regulation of ICAM-1 in S. pneumoniae AOM

ICAM-1 exists in two forms: a membrane form (mICAM-1) and a soluble form. mICAM-1 produces the soluble form of ICAM-1 by undergoing proteolysis (Budnik et al. 1996. Analysis of the production of soluble ICAM-1 molecules by human cells. Exp. Hematol. 24:352-359). The level of the soluble form of ICAM-1 is increased during inflammation in proportion to the level of mICAM-1. To study transcriptome regulation of ICAM-1, one child was randomly selected from whom PBMCs were obtained at a time of health, during AOM caused by S. pneumoniae, and during convalescence. It was found that the ICAM-1 gene from PBMCs was upregulated 2.52 times during AOM compared with the level of regulation at the preinfection carriage stage. In the convalescent stage after treatment, the ICAM-1 gene was downregulated 10.21 times compared with the level of regulation during AOM (Table 1). To verify the results of microarray analysis, the total RNAs were extracted from PBMCs derived from 6 children and qRTPCR was performed with ICAM-1-specific primers. Similar to the microarray analysis, the mean levels of ICAM-1 in 6 children with AOM caused by S. pneumoniae were upregulated 2.8-fold compared to the levels during the healthy stage. After successful treatment of AOM, the expression of the ICAM-1 gene was reduced to 1.1-fold compared to that during AOM caused by the S. pneumoniae (Table 1). Thus, the transcriptome pattern was similar to that observed in the serum sICAM-1 obtained via ELISA.

TABLE 1

Expression of ICAM-1 at transcriptional level[a]

| Method | No. of patients | Fold change | |
|---|---|---|---|
| | | AOM/carri. | AOM/conval. |
| Microarray | 1 | 2.25 | 10.21 |
| qRT-PCR | 6 | 2.76 | 1.13 |

[a]Total RNA was extracted from peripheral blood mononuclear cells from the same child at three time points: at the time of AOM caused by S. pneumoniae, before the S. pneumoniae infection (carriage [carri.]), and after the infection during the convalescent (conval.) stage. Microarray analysis and qRT-PCR were performed as described in Materials and Methods. Data were analyzed after normalization (see Materials and Methods). The data for qRT-PCR are the mean of 6 children.

d) Discussion

The present study shows that serum levels of sICAM-1 are significantly higher in S. pneumoniae-, nontypeable H. influenzae-, and M. catarrhalis AOM-infected children than in well children, confirming that a systemic inflammatory response occurs during AOM; that sICAM-1 levels vary from no elevation to high elevations among children with AOM; that in paired samples the sICAM-1 levels increase when children develop AOM due to S. pneumoniae compared to their sICAM-1 levels before infection; and that the level of sICAM-1 returns to pre-AOM levels during the convalescent stage of AOM after successful antimicrobial therapy. When children develop AOM due to nontypeable H. influenzae, however, significant increases in sICAM-1 levels are not detected. The levels of sICAM-1 in healthy children at ages 6, 12, 15, 18, 24, and 30 months, during NP carriage of otopathogens with and without concurrent viral upper respiratory infections was also evaluated, and it was found that neither the age of the child nor the presence of a viral URI impacted serum sICAM-1 levels in the study population. In addition, transcription regulation of ICAM-1 was evaluated in AOM caused by S. pneumoniae. It is believed that this is the first report on the detailed changes of sICAM-1 levels in the sera of children with AOM.

Similar to the erythrocyte sedimentation and C-reactive protein, ICAM-1 is inducible by proinflammatory mediators and by bacterial products in association with bacterial infection. It is well documented that ICAM-1 is endogenously expressed on various cell types and makes possible reversible adhesion and signal transduction between cells, processes critical to T cell development. Increased levels of ICAM-1 promote cell-cell interactions, playing a critical role in leukocyte recruitment and leading to prolonged and, sometimes, excessive inflammation (Xie et al. 2008. Moraxella catarrhalis lipooligosaccharide selectively upregulates ICAM-1 expression on human monocytes and stimulates adjacent naïve monocytes to produce TNF-alpha through cellular crosstalk. Cell. Microbiol. 10:1453-1467).

This study focused on children ages 6 to 30 months with AOM, and compared the sICAM-1 levels in the sera of children with AOM and the sera of healthy children; in the sera of children whose NPs were colonized and in the sera of children whose NPs were not colonized with potential AOM otopathogens; as well as in the sera of individual children obtained pre-AOM, at the time of AOM, and during convalescence from AOM. The mean levels of serum sICAM-1 in healthy children whose NPs were colonized and not colonized with otopathogens were found to be the same, measured as a mean of 232 ng/ml. This quantity is similar to the serum sICAM-1 levels in healthy adults ages 20 to 50 years (203 ng/ml) (Biesiada et al. 2009. Levels of sVCAM-1 and sICAM-1 in patients with Lyme disease. Pol. Arch. Med. Wewn. 119:200-204). At the time of onset of AOM in the children, the serum levels of sICAM-1 were studied and found that they increased 2.1 times compared with the level in the healthy controls to a mean level of about 500 ng/ml, a level similar to those obtained during other infectious diseases (Chihara et al. 1994. Soluble ICAM-1 in sputum of patients with bronchial asthma. Lancet 343:1108, Terada et al. 1993. Serum level of soluble ICAM-1 in subjects with nasal allergy and ICAM-1 mRNA expression in nasal mucosa. Jpn. J. Allergol. 42:87-93). With effective antibiotic treatment and clinical resolution of AOM, it was found that serum sICAM-1 returned to preinfection levels. These results suggest that the inflammatory reaction in the middle ear during bacterial AOM is associated with a systemic inflammatory response and that after recovery from AOM the decrease in the levels of sICAM-1 in the sera reflect a resolution of inflammation.

Serum sICAM-1 levels varied widely among children with AOM in this study. The subjects whom were studied were selected on the basis of the bacterial species causing AOM; they were otherwise healthy, except for concurrent clinically diagnosed viral upper respiratory infections, and had no other infections or diseases. Two possibilities contributing to this variation that might be considered were the severity of the disease and the age of the child. All the children in the current study had bulging tympanic membranes, suggestive of a clearly established AOM. However, there is no recognized system to score the severity of AOM. Methods used to classify AOM, such as symptoms (questionnaire from parents), body temperature, and signs (on otoscopy examination) are subjective. For example, the severity of ear pain depends on an individual's pain sensitivity threshold. Therefore, an analysis of the association between symptoms and signs and sICAM-1 levels was not performed. Recently, it was found that the adaptive immune response to NP carriage of otopathogens increases with age in the study cohort (Casey, J. R., and M. E. Pichichero. 2004. Changes in frequency and pathogens causing acute otitis media in 1995-2003. Pediatr. Infect. Dis. J. 23:824-828), and others have found an association of younger age and susceptibility to AOM (Passariello et al. 2006 Rhinoviruses promote internalisation of Staphylococcus aureus into non-fully permissive cultured pneumocytes. Microbes Infect. 8:758-766.), so variations in sICAM-1 levels were evaluated according to the age of the child at the time of AOM. It was found that when children experienced AOM when they were under the age of 18 months, they had lower sICAM-1 levels than 18- to 23-month old children. Witkowska et al. (Witkowska et al. 2006. Relationship among TNF-α, sICAM-1, and selenium in presurgical patients with abdominal aortic aneurysms. Biol. Trace Element Res. 114:31-40) reported that there was no difference in serum sICAM-1 levels in adults ages 42 to 81 years with abdominal aortic aneurysms. El-Sawy et al. (El-Sawy et al 1999. Soluble intercellular adhesion molecule-1 in sera of children with bronchial asthma exacerbation. Int. Arch. Allergy Immunol. 119:126-132) did not find any difference in serum sICAM-1 levels in children ages 6 to 12 years with bronchial asthma exacerbations.

Serum sICAM-1 levels showed a dynamic change during AOM progression, and that the change in S. pneumoniae infection appeared to be different from that in nontypeable H. influenzae infection. Although AOM is usually treated as a single entity, both studies with humans and experimental animal studies suggest that there are differences in host responses, depending on the organism involved (Heikkinen et al. 1998. Serum interleukin-6 in bacterial and nonbacterial acute otitis media. Pediatrics 102:296-299, 29, 36). There are indications that nontypeable H. influenzae antigens evoke a greater local inflammatory response than pneumococcal antigens (Miller et al. 1990. Bacterial antigens and neutrophil granule proteins in middle ear effusions. Arch. Otolaryngol. Head Neck Surg. 116:335-337). However, there is no report on the serum level change of sICAM-1 in nontypeable H. influenzae-infected children with AOM. S. pneumoniae infection, on the other hand, is clinically more severe and involves a higher risk of serious disease and intracranial complications (Barry et al. 1999. Otogenic intracranial infections in adults. Laryngoscope 109:483-487; Petersen et al. 1998. Acute mastoidectomy in a Danish county from 1977-1996 with focus on the bacteriology. Int. J. Pediatr. Otorhinolaryngol. 45:21-29; Rudberg, R. D. 1954. Acute otitis media: comparative therapeutic results of sulphonamide and penicillin administered in various forms. Acta Otolaryngol. (Stockholm) 113(Suppl.):9-79). S. pneumoniae induces better systemic protection against reinfections than do nontypeable H. influenzae and M. catarrhalis (Branefors-Helander et al. 1975. Acute otitis media. A clinical, bacteriological and serological study of children with frequent episodes of acute otitis media. Acta Otolaryngol. (Stockholm) 80:399-409; Klein, J. O. 1994. Otitis media. Clin. Infect. Dis. 19:823-833; Murphy, T. F. 1996. Branhamella catarrhalis: epidemiology, surface antigenic structure, and immune response. Microbiol. Rev. 60:267-279). However, this study shows that the levels of sICAM-1 in children with AOM infected by S. pneumoniae, nontypeable H. influenzae, or M. catarrhalis are similar. In addition, we found the levels of sICAM-1 in the sera of children infected by nontypeable H. influenzae were higher than those in the sera of healthy children (P<0.05); however, there was no significant change during the progression of AOM in the same child at the three stages. Animal experiments showed that AOM appears 1 day after nontypeable H. influenzae inoculation and 3 days after S. pneumoniae inoculation and that lower transcript levels of cytokines such as interleukin-6 (IL-6), IL-1alpha, tumor necrosis factor alpha, and IL-10 were detected in S. pneumoniae-infected animals than in nontypeable H. influenzae infected animals (Melhus, A., and A. F. Ryan. 2000. Expression of cytokine genes during pneumococcal and nontypeable Haemophilus influenzae acute otitis media in the rat. Infect. Immun. 68:4024-4031). Genetic analysis showed that variation in innate immunoresponse genes, such as the TNFA-863A, TNFA-376G, TNFA-238G, IL-10-1082A, and IL-6-174G alleles, might result in altered cytokine production that leads to altered inflammatory responses (Emonts et al. 2007. Genetic polymorphisms in immunoresponse genes TNFA, IL6, IL10, and TLR4 are associated with recurrent acute otitis media. Pediatrics 120:814-823) and, hence, can contribute to altered ICAM-1 levels as well. The relationship between ICAM-1 alleles and disease susceptibility in other diseases has been reported. For example, a mutation of the coding region of ICAM-1, ICAM-1Kilifi, causing a change from Lys to Met in the loop region, increased the susceptibility of Kenyan children to severe malaria (Kun et al. 1999. Association of the ICAM-1Kilifi mutation with protection against severe malaria in Lambarene, Gabon. Am. J. Trop. Med. Hyg. 61:776-779). Matsuzawa et al. found that the allelic frequency of K469E was significantly higher both in patients with Crohn's disease and in patients with ulcerative colitis than in controls (Matsuzawa et al 2003. Association between K469E allele of intercellular adhesion molecule 1 gene and inflammatory bowel disease in a Japanese population. Gut 52:75-78). ICAM-1 genotype GIG (corresponding to Lys469G1u) exhibited a higher frequency in patients with grade II astrocytomas (Burim et al. 2009. ICAM-1 (Lys469Glu) and PECAM-1 (Leu125Val) polymorphisms in diffuse astrocytomas. Clin. Exp. Med. 9:157-163). Therefore, the finding of no significant difference in sICAM-1 levels in nontypeable *H. influenzae* infected children during AOM and during their preinfection carrier stage can be influenced by genetic factors such as ICAM-1 gene polymorphisms.

Serum levels of sICAM-1 did not appear to vary in magnitude in healthy children of various ages (between 6 and 30 months). El-Sawy et al. (1999. Soluble intercellular adhesion molecule-1 in sera of children with bronchial asthma exacerbation. Int. Arch. Allergy Immunol. 119:126-132) and Abdelrazik et al. (2008. Serum level of intercellular adhesion molecule-1 in children with malignant lymphoma. Med. Princ. Pract. 17:233-238.) reported that no significant correlation was found between age and serum sICAM-1 levels in healthy children at the ages of 6 to 12 years. The results presented herein are consistent with their observations. Serum levels of sICAM-1 in healthy children did not appear to vary during NP colonization with otopathogens. This is consistent with the clinical observation of an absence of signs of inflammation in the nasal mucosa when otopathogen colonization occurs. In addition, since the subjects studied in the present study were selected on the basis of the presence of AOM caused by different otopathogens and subjects with other infections, chronic diseases, and other diseases were excluded, the main clinical context where AOM must be differentiated from a second infection is the circumstance where a viral URI is occurring simultaneously. Therefore, the sICAM-1 levels of children with viral URIs but without AOM were studied. It was found that the serum levels of sICAM-1 did not vary during viral URIs in this study population. There are previous reports on the upregulation of sICAM-1 after infection by respiratory viruses in vitro (Chini et al. 1998. Essential roles of NF-kB and C/EBP in the regulation of intercellular adhesion molecule-1 after respiratory syncytial virus infection of human respiratory epithelial cell cultures. J. Virol. 72:1623-1626; Gao et al. 2000. Human parainfluenza virus type 3 upregulates ICAM-1 (CD54) expression in a cytokineindependent manner. Gene Expr. 9:115-121). However, observations in vivo were different from the results obtained in vitro. Lai et al. (Lai et al. 2004. Elevated levels of soluble adhesion molecules in sera of patients with acute bronchiolitis J. Microbiol. Immunol. Infect. 37:153-156) found that mean sICAM-1 concentrations were similar between respiratory syncytial virus (RSV)-positive and RSV-negative patients with acute bronchiolitis. Kosai et al. (Kosai et al. 2008. Elevated levels of high mobility group box chromosomal protein-1 (HMGB-1) in sera from patients with severe bacterial pneumonia coinfected with influenza virus. Scand. J. Infect. Dis. 40:338-342) tested plasma levels of sICAM-1 in patients with bacterial pneumonia coinfected with influenza virus and those not coinfected. They found similar levels of sICAM-1 in the two groups.

The elevation of ICAM-1 levels caused by infection with otopathogens has been previously reported in vitro. A recent study showed that *M. catarrhalis* lipooligosaccharide (LOS) stimulates proinflammatory cytokine production and selectively induces ICAM-1 expression on human monocytes via Toll-like receptor 4 (TLR4)-dependent and CD14-dependent pathways (Xie, H., and X. X. Gu. 2008. *Moraxella catarrhalis* lipooligosaccharide selectively upregulates ICAM-1 expression on human monocytes and stimulates adjacent naïve monocytes to produce TNF-alpha through cellular crosstalk. Cell. Microbiol. 10:1453-1467). Avadhanula et al. found that nontypeable *H. influenzae* infection increased the level of ICAM-1 expression on carcinomic human alveolar basal epithelial (A549) cells invitro (Avadhanula et al. 2006. Nontypeable *Haemophilus influenzae* adheres to intercellular adhesion molecule 1 (ICAM-1) on respiratory epithelial cells and upregulates ICAM-1 expression. Infect. Immun. 74:830-838). Limited information on sICAM-1 expression in humans with chronic serous and mucoid otitis media has been previously described. Himi et al. (Himi et al. 1994. Quantitative analysis of soluble cell adhesion molecules in otitis media with effusion. Acta Otolaryngol. (Stockholm) 114:285-288) measured the levels of sICAM-1 in MEEs of children with chronic serous and mucoid otitis media and found that MEEs contained significantly higher levels of sICAM-1 than the sera of healthy children, but they did not comparatively study serum sICAM-1 levels in children with chronic serous otitis media and children with mucoid otitis media (Himi et al. 1994. Quantitative analysis of soluble cell adhesion molecules in otitis media with effusion. Acta Otolaryngol. (Stockholm) 114:285-288). Russo et al. studied the ICAM-1 levels in middle ear serous and mucoid effusions in children with otitis media with effusion (a clinical condition distinctly different from AOM) and did not find elevated levels (Russo et al. 2004. Cell adhesion molecules and cytokines in middle ear effusions in children with or without recent acute otitis media. Otolaryngol. Head Neck Surg. 130:242-248). Ganbo et al. (1995. Inhibition of mucociliary clearance of the eustachian tube by leukotriene C4 and D4. Ann. Otol. Rhinol Laryngol. 104:231-236) also studied the levels of sICAM-1 in MEEs of subjects ages 3 to 79 years with mucoid otitis media and found that the mean level of sICAM-1 was 1,440 ng/ml, whereas the mean level in the MEEs of subjects with serous otitis media was 430 ng/ml. In this study we focused on the serum sICAM-1 expression levels in children with AOM and the relationship between sICAM-1 levels and the infecting organism as well as the dynamic change in ICAM-1 levels during the process of AOM development. Because chronic serous and mucoid otitis media are pathological conditions very different from AOM, no direct comparison of the significance of sICAM-1 levels in MEEs or sera from those populations and ours is biologically relevant.

Passariello et al. have demonstrated that the significant enhancement of *S. aureus* infections following human rhinovirus (HRV) infections in vitro is mediated by the enhanced levels of inflammatory cytokines released from HRV-infected cells and the subsequent overexpression of ICAM-1 (Passariello et al. 2006 Rhinoviruses promote internalization of *Staphylococcus aureus* into non-fully permissive cultured pneumocytes. Microbes Infect. 8:758-766). The phenomenon could be prevented by blocking ICAM-1 or IL-6 and IL-8 activities with neutralizing antibodies (Passariello et al. 2006 Rhinoviruses promote internalization of *Staphylococcus aureus* into non-fully permissive cultured pneumocytes. Microbes Infect. 8:758-766). In vitro, by upregulation of expression of ICAM-1, RSV and influenza virus promote nontypeable *H. influenzae* and *S. pneumoniae* colonization of the NPs and adherence of these bacteria to respiratory epithelial cells (Avadhanula et al. 2007. Nontypeable *Haemophilus influenzae* and *Streptococcus pneumoniae* bind respiratory syncytial virus glycoprotein, J. Med. Microbiol. 56:1133-1137). Moreover, ICAM-1 can promote the uptake of bacterial pathogens by macrophages and increase neutrophil recruitment (Humlicek et al. 2004. Modulation of airway inflammation and bacterial clearance by epithelial cell ICAM-1. Am. J. Physiol. Lung Cell. Mol. Physiol. 287:L598-L607; O'Brien et al. 1999. Role of alveolar epithelial cell intercellular adhesion molecule-1 in host defense against *Klebsiella pneumoniae*. Am. J. Physiol. 276:L961-L970.). Frick et al. (2000. *Haemophilus influenzae* stimulates ICAM-1 expression on respiratory epithelial cells. J. Immunol. 164:4185-4196) and Humlicek et al. (2004. Modulation of airway inflammation and bacterial clearance by epithelial cell ICAM-1. Am. J. Physiol. Lung Cell. Mol. Physiol. 287:L598-L607) found that adherence of nontypeable *H. influenzae* to respiratory epithelial cells rapidly induced ICAM-1 expression, a process that they hypothesized would facilitate the recruitment of neutrophils to sites of nontypeable *H. influenzae* infection. Xie and Gu demonstrated that leukocyte recruitment mediated by enhanced ICAM-1 levels after *M. catarrhalis* infection may also result in increased bacterial adhesion to the respiratory tract (Xie, H., and X. X. Gu. 2008. *Moraxella catarrhalis* lipooligosaccharide selectively upregulates ICAM-1 expression on human monocytes and stimulates adjacent naïve monocytes to produce TNF-alpha through cellular crosstalk. Cell. Microbiol. 10:1453-1467). In the current study, although there is no direct evidence to illustrate that the enhanced ICAM-1 level has promoted neutrophil recruitment to the middle ear, the literature and the fact that the elevation of serum sICAM-1 levels in children with AOM positive for bacteria in MEF indicate that the intercellular adhesion molecules are upregulated during middle ear inflammation and that the increased ICAM-1 levels may contribute to innate immune responses through increasing leukocyte recruitment to the middle ear.

In conclusion, it is demonstrated herein that the elevation of serum sICAM-1 levels in children with AOM is correlated to pathogen presence and an inflammatory reaction in the middle ear. Moreover, the study raises new questions about the role of the sICAM-1 level during otopathogen infection, and answers to those questions can help develop and introduce early interventions to moderate the acute inflammatory process and abort disease progression from colonization in the respiratory system (NPs) to AOM.

REFERENCES

Abdelrazik, N., M. Fouda, M. H. Zaghloul, and D. Abbas. 2008. Serum level of intercellular adhesion molecule-1 in children with malignant lymphoma. Med. Princ. Pract. 17:233-238. American Academy of Pediatrics. 2004. Subcommittee on Management of Acute Otitis Media. Diagnosis and management of acute otitis media. Pediatrics 113: 1451-1465.

Abramson, J. S., and J. G. Wheeler. 1994. Virus-induced neutrophil dysfunction: role in the pathogenesis of bacterial infections. Pediatr. Infect. Dis. J. 13:643-652.

Abramson, J. S., G. S. Giebink, and P. G. Quie. 1982. Influenza A virus induced polymorphonuclear leukocyte dysfunction in the pathogenesis of experimental pneumococcal otitis media. Infect. Immun. 36:289-296.

Amiri, M. V., S. D. Mansoori, M. Shekar-Abi, S. M. Mirsaeidi, S. Zahirifard, M. K. Dizaji, P. Tabarsi, A. Halvani, S. D. Tabatabaee, and M. R. Masjedi. 2004. SICAM-1 as a serum marker for follow-up of pulmonary tuberculosis therapy. Tanaffos 3:55-63.

Arola, M., Ruuskanen, O., Ziegler, T., Mertsola, j., Nanto-Salonen, K. et al Clinical role of respiratory virus infection in acute otitis media. (1990) Pediatr. 86, 848-55.

Avadhanula, V., C. A. Rodriguez, G. C. Ulett, L. O. Bakaletz, and E. E. Adderson. 2006. Nontypeable *Haemophilus influenzae* adheres to intercellular adhesion molecule 1 (ICAM-1) on respiratory epithelial cells and upregulates ICAM-1 expression. Infect. Immun. 74:830-838.

Avadhanula, V., Y. Wang, A. Portner, and E. Adderson. 2007. Nontypeable *Haemophilus influenzae* and *Streptococcus pneumoniae* bind respiratory syncytial virus glycoprotein, J. Med. Microbiol. 56:1133-1137.

Barry, B., J. Delattre, F. Vie, J. P. Bedos, and P. Gehanno. 1999. Otogenic intracranial infections in adults. Laryngoscope 109:483-487.

Basta G, Sironi A M, Lazzerini G, Del Turco S, Buzzigoli E, Casolaro A, Natali A, Ferrannini E, Gastaldelli A (2006) Circulating soluble receptor for advanced glycation end products is inversely associated with glycemic control and S100A12 protein. J Clin Endocrinol Metab 91:4628-4634.

Baumer, I., G. Zissel, M. Schlaak, and J. Muller-Quernheim. 1998. Soluble intercellular adhesion molecule 1 (sICAM-1) in bronchoalveolar lavage (BAL) cell cultures and in the circulation of patients with tuberculosis, hypersensitivity pneumonitis and sarcoidosis. Eur. J. Med. Res. 3:288-294.

Bianchi M E (2007) DAMPs, PAMPs and alarmins: all we need to know about danger. J Leukoc Biol 81:1-5.

Biesiada, G., J. Czepiel, I. Sobczyk-Krupiarz, D. Salamon, A. Garlicki, and T. Mach. 2009. Levels of sVCAM-1 and sICAM-1 in patients with Lyme disease. Pol. Arch. Med. Wewn. 119:200-204.

Branefors-Helander, P., T. Dahlberg, and O. Nyle'n. 1975. Acute otitis media. A clinical, bacteriological and serological study of children with frequent episodes of acute otitis media. Acta Otolaryngol. (Stockholm) 80:399-409.

Broides, Amon; Leibovitz, Eugene; Dagan, Ron; Press, Joseph; Raiz, Simon; Kafka, Michael; Leiberman, Albrebo; Yermiahu, Tikva. Cytology of middle ear fluid during acute otitis media, Pediatric Infectious Disease Journal: 2002, 21(1):57-60.

Bryan W T K. The identification and clinical significance of large phagocyte in exudates of acute otitis media and mastoiditis. Laryngoscope 1953; 63:559.

Budnik, A., M. Grewe, K. Gyufko, and J. Krutmann. 1996. Analysis of the production of soluble ICAM-1 molecules by human cells. Exp. Hematol. 24:352-359.

Buhimschi I A, Zhao G, Pettker C M, Bahtiyar M O, Magloire L K, Thung S, Fairchild T, Buhimschi C S (2007) The receptor for advanced glycation end products (RAGE) system in women with intraamniotic infection and inflammation. Am J Obstet Gynecol. 196:181.

Burim, R. V., S. A. Teixeira, B. O. Colli, F. M. Peria, L. F. Tirapelli, S. K. Marie, S. M. Malheiros, S. M. Oba-Shinjo, A. A. Gabbai, P. A. Lotufo, and C. G. Carlotti-Ju'nior. 2009. ICAM-1 (Lys469Glu) and PECAM-1 (Leu125Val) polymorphisms in diffuse astrocytomas. Clin. Exp. Med. 9:157-163.

Casey, J. R., and M. E. Pichichero. 2004. Changes in frequency and pathogens causing acute otitis media in 1995-2003. Pediatr. Infect. Dis. J. 23:824-828.

Casey, J. R., D. G. Adlowitz, and M. E. Pichichero. 2010. New patterns in the otopathogens causing acute otitis media six to eight years after introduction of pneumococcal conjugate vaccine. Pediatr. Infect. Dis. J. 29:304-309.

Chandler, S. M., S. M. Garcia, and D. P. McCormick. 2007. Consistency of diagnostic criteria for acute otitis media: a review of the recent literature. Clin. Pediatr. (Phila.) 46:99-108.

Chihara, J., T. Yamamoto, D. Kurachi, and S, Nakajima. 1994. Soluble ICAM-1 in sputum of patients with bronchial asthma. Lancet 343:1108.

Chini, B. A., M. A. Fiedler, L. Milligan, T. Hopkins, and J. M. Stark. 1998. Essential roles of NF-kB and C/EBP in the regulation of intercellular adhesion molecule-1 after respiratory syncytial virus infection of human respiratory epithelial cell cultures. J. Virol. 72:1623-1626.

Cotran; Kumar, Collins (1998). Robbins Pathologic Basis of Disease. Philadelphia: W.B Saunders Company. ISBN 0-7216-7335-X.

Cristino J M (1999) Correlation between consumption of antimicrobials in humans and development of resistance in bacteria. Int J Antimicrob Agents 12:199-202.

El-Savvy, I. H., O. M. Badr-El-Din, O. E. El-Azzouni, and H. A. Motawae. 1999. Soluble intercellular adhesion molecule-1 in sera of children with bronchial asthma exacerbation. Int. Arch. Allergy Immunol. 119:126-132.

Emonts, M., R. H. Veenhoven, S. P. Wiertsema, J. J. Houwing-Duistermaat, V. Walraven, R. de Groot, P. W. M. Hermans, and E. A. Sanders. 2007. Genetic polymorphisms in immunoresponse genes TNFα, IL6, IL10, and TLR4 are associated with recurrent acute otitis media. Pediatrics 120: 814-823.

Faden, H., L. Brodsky, J. Bernstein, J. Stanievich, D. Krystofik, et al. 1989. Otitis media in children: local immune response to nontypeable *Haemophilus influenzae*. Infect. Immun. 57:3555-3559.

Foell D, Herna'ndez-Rodn'guez J, Sa'nchez M, Vogl T, Cid M C, Roth J (2004a) Early recruitment of phagocytes contributes to the vascular inflammation of giant cell arteritis. J Pathol 204:311-316.

Foell D, Ichida F, Vogl T, Yu X, Chen R, Miyawaki T, Sorg C, Roth J.: S100A12 (EN-RAGE) in monitoring Kawasaki disease. Lancet. 361: 1270-2, 2003b.

Foell D, Kucharzik T, Kraft M, Vogl T, Sorg C, Domschke W, Roth J. Neutrophil derived human S100A12 (EN-RAGE) is strongly expressed during chronic active inflammatory bowel disease. Gut. 2003a Jun; 52(6):847-53.

Foell D, Seeliger S, Vogl T, Koch H G, Maschek H, Harms E, Sorg C, Roth J.: Expression of S100A12 (EN-RAGE) in cystic fibrosis. Thorax. 58: 613-617, 2003c.

Foell D, Wittkowski H, Hammerschmidt I, Wulffraat N, Schmeling H, Frosch M, Horneff G, Kuis W, Sorg C, Roth J. Monitoring neutrophil activation in juvenile rheumatoid arthritis by S100A12 serum concentrations. Arthritis Rheum. 2004b, 50: 1286-95.

Foell D, Wittkowski H, Roth J (2007a) Mechanisms of disease: a 'DAMP' view of inflammatory arthritis. Nat Clin Pract Rheumatol 3:382-390.

Foell D, Wittkowski H, Vogl T, Roth J (2007b) S100 proteins expressed in phagocytes: a novel group of damage-associated molecular pattern molecules. J Leukoc Biol 81:28-37.

Frick, A. G., T. D. Joseph, L. Pang, A. M. Rabe, J. W. St Geme III, and D. C. Look. 2000. *Haemophilus influenzae* stimulates ICAM-1 expression on respiratory epithelial cells. J. Immunol. 164:4185-4196.

Froom J, Culpepper L, Jacobs M, DeMelker R A, Green L A, van Buchem L (1997) Antimicrobials for acute otitis media? A review from the International Primary Care Network. BMJ 315:98-102.

Ganbo, T., K. Hisamatsu, S. Shimomura, T. Nakajima, H. Inoue, and Y. Murakami. 1995. Inhibition of mucociliary clearance of the eustachian tube by leukotriene C4 and D4. Ann. Otol. Rhinol Laryngol. 104:231-236.

Gao, J., S. Choudhary, A. K. Banerjee, and B. P. De. 2000. Human parainfluenza virus type 3 upregulates ICAM-1 (CD54) expression in a cytokineindependent manner. Gene Expr. 9:115-121.

Gates G A: Cost-effectiveness considerations in otitis media treatment. *Otolaryngol Head Neck Surg* 1996, 114: 525-530.

Giebink G S, Juhn S K, Weber M L, Le C T. The bacteriology and cytology of chronic otitis media with effusion. Pediatr Infect Dis. 1982 March-April; 1(2):98-103.

Gottsch J D, Liu S H (1998) Cloning and expression of human corneal calgranulin C(CO—Ag). Curr Eye Res 17:870-874.

Gottsch J D, Stark W J, Liu S H (1997) Cloning and sequence analysis of human and bovine corneal antigen (CO—Ag) cDNA: identification of host-parasite protein calgranulin C. Trans Am Ophthalmol Soc 95:111-125.

Greenberg, D. P. and Alejandro Hoberman. Vaccine Prevention of Acute Otitis Media, Current Allergy and Asthma Reports 2001, 1:358-363.

Guignard F, Mauel J, Markert M (1995) Identification and characterization of a novel human neutrophil protein related to the S100 family. Biochem J 309:395-401.

Heikkinen, T., F. Ghaffar, A. O. Okorodudu, and T. Chonmaitree. 1998. Serum interleukin-6 in bacterial and nonbacterial acute otitis media. Pediatrics 102:296-299.

Henderson, F. W., Collier, A. M., Sanyal, M. & Watkins, J. M. et al. (1982) Viral-Bacterial Synergistic Interaction in the Pathogenesis of Otitis Media in Aboriginal Children. N Engl 1 Med. 306, 1379-83.

Himi, T., M. Kamimura, A. Kataura, and K. Imai. 1994. Quantitative analysis of soluble cell adhesion molecules in otitis media with effusion. Acta Otolaryngol. (Stockholm) 114:285-288.

Hitomi J, Kimura T, Kusumi E, Nakagawa S, Kuwabara S, Hatakeyama K, Yamaguchi K (1998) Novel S100 proteins in human esophageal epithelial cells: CAAF1 expression is associated with cell growth arrest. Arch Histol Cytol 61:163-178.

Hitomi J, Yamaguchi K, Kikuchi Y, Kimura T, Maruyama K, Nagasaki K (1996) A novel calcium-binding protein in amniotic fluid, CAAF1: its molecular cloning and tissue distribution. J Cell Sci 109: 805-815

Hofmann M A, Drury S, Fu C, Qu W, Taguchi A, Lu Y, Avila C, Kambham N, Bierhaus A, Nawroth P, Neurath M F, Slattery T, Beach D, McClary J, Nagashima M, Morser J, Stern D, Schmidt A M (1999) RAGE mediates a novel proinflammatory axis: a central cell surface receptor for S100/calgranulin polypeptides. Cell 97:889-901.

Howie, V. M., R. Dillard, and B. Lawrence. 1985. In vivo sensitivity test in otitis media: efficacy of antibiotics. Pediatrics 75:8-13.

Humlicek, A. L., L. Pang, and D. C. Look. 2004. Modulation of airway inflammation and bacterial clearance by epithelial cell ICAM-1. Am. J. Physiol. Lung Cell. Mol. Physiol. 287:L598-L607.

Jaber, S. M., E. A. Hamed, and S. A Hamed. 2009. Adhesion molecule levels in serum and cerebrospinal fluid in children with bacterial meningitis and sepsis. J. Pediatr. Neurosci. 4:76-85.

Kamimura M, Himi T, Yosioka I, Kataura A. Adhesion molecules in immune-mediated otitis media with effusion. In: Lim D J, editor. Abstracts of the sixth international symposium on recent advances in otitis media. Ft. Lauderdale (FL): 1995, 193-195.

Kaur, R., D. G. Adlowitz, J. R. Casey, M. Zeng, and M. E. Pichichero. 23 Mar. 2010. Simultaneous assay for four bacterial species including Alloiococcus otitidis using multiplex-PCR in children with culture negative acute otitis media. Pediatr. Infect. Dis. J. 2010 29(8):741-5.

Keiichi Ichimura*"Neutrophil chemotaxis in children with recurrent otitis media. International Journal of Pediatric Otorhinolaryngology Volume 4, Issue 1, 1982, 47-55.

Kim M H, Choi Y W, Choi H Y, Myung K B, Cho S N (2006) The expression of RAGE and EN-RAGE in leprosy. Br J Dermatol 154:594-601

Klein, J. O. 1994. Otitis media. Clin. Infect. Dis. 19:823-833.

Kosai, K., M. Seki, K. Yanagihara, S, Nakamura, S. Kurihara, K. Izumikawa, H. Kakeya, Y. Yamamoto, T. Tashiro, and S. Kohno. 2008. Elevated levels of high mobility group box chromosomal protein-1 (HMGB-1) in sera from patients with severe bacterial pneumonia coinfected with influenza virus. Scand. J. Infect. Dis. 40:338-342.

Kosaki A, Hasegawa T, Kimura T, Iida K, Hitomi J, Matsubara H, Mori Y, Okigaki M, Toyoda N, Masaki H, Inoue-Shibata M, Nishikawa M, Iwasaka T (2004) Increased plasma S100A12 (EN-RAGE) levels in patients with type 2 diabetes. J Clin Endocrinol Metab 89:5423-5428.

Kun, J. F., J. Klabunde, B. Lell, D. Luckner, M. Alpers, J. May, C. Meyer, and P. G. Kremsner. 1999. Association of the ICAM-1Kilifi mutation with protection against severe malaria in Lambarene, Gabon. Am. J. Trop. Med. Hyg. 61:776-779.

Lai, C.-C., H.-Y. Tai, H.-D. Shen, W.-T. Chung, R.-L. Chung, and R.-B. Tang. 2004. Elevated levels of soluble adhesion molecules in sera of patients with acute bronchiolitis J. Microbiol. Immunol. Infect. 37:153-156.

Larsen A, Bronstein I B, Dahl O, Wentzel-Larsen T, Kristoffersen E K, Fagerhol MK (2007) Quantification of S100A12 (EN-RAGE) in blood varies with sampling method, calcium and heparin. Scand J Immunol 65:192-201

Liao H, Wu J, Kuhn E, Chin W, Chang B, Jones M D, O'Neil S, Clauser K R, Karl J, Hasler F, Roubenoff R, Zolg W, Guild B C (2004) Use of mass spectrometry to identify protein biomarkers of disease severity in the synovial fluid and serum of patients with rheumatoid arthritis. Arthritis Rheum 50:3792-3803

Liu, Keyi, and Michael Pichichero. Transcriptome profile of peripheral blood mononuclear cells in children with acute otitis media caused by *Streptococcus pneumoniae*. Genes and Immunity, 2010. Submitted Liu, Keyi, Janet Casey and Michael Pichichero. Serum Intercellular Adhesion Molecule 1 Variations in Young Children During Acute Otitis Media. Clinical and vaccine immunology, 2010. Accepted Lysenko E S, Ratner A J, Nelson A L, Weiser J N (2005). "The role of innate immune responses in the outcome of interspecies competition for colonization of mucosal surfaces". PLoS Pathog 1 (1): el.

Marti T, Erttmann K D, Gallin M Y (1996) Host-parasite interaction in human onchocerciasis: identification and sequence analysis of a novel human calgranulin. Biochem Biophys Res Commun 221:454-458

Matsuzawa, J., K. Sugimura, Y. Matsuda, M. Takazoe, K. Ishizuka, T. Mochizuki, S. S. Seki, O. Yoneyama, H. Bannnai, K. Suzuki, T. Honma, and H. Asakura. 2003. Association between K469E allele of intercellular adhesion molecule 1 gene and inflammatory bowel disease in a Japanese population. Gut 52:75-78.

Me'garbane, B., P. Marchal, A. Marfaing-Koka, O. Belliard, F. Jacobs, I. Chary, et al. 2004. Increased diffusion of soluble adhesion molecules in meningitis, severe sepsis and systemic inflammatory response without neurological infection is associated with intrathecal shedding in cases of meningitis. Intensive Care Med. 30:867-874.

Melhus, A., and A. F. Ryan. 2000. Expression of cytokine genes during pneumococcal and nontypeable *Haemophilus influenzae* acute otitis media in the rat. Infect. Immun. 68:4024-4031.

Miller, M. B., P. J. Koltai, and S. V. Hetherington. 1990. Bacterial antigens and neutrophil granule proteins in middle ear effusions. Arch. Otolaryngol. Head Neck Surg. 116:335-337.

Murphy, T. F. 1996. *Branhamella catarrhalis*: epidemiology, surface antigenic structure, and immune response. Microbiol. Rev. 60:267-279.

Naylor, E. J., Denise Bakstad, Mark Biffen, Bob Thong, Peter Calverley, Stephen Scott, C. Anthony Hart, Robert J. Moots, and Steven W. Edwards. *Haemophilus influenzae* Induces Neutrophil Necrosis A Role in Chronic Obstructive Pulmonary Disease? Am J Respir Cell Mol Biol Vol 37. pp 135-143, 2007.

O'Brien, A. D., T. J. Standiford, K. A. Bucknell, S. E. Wilcoxen, and R. Paine III. 1999. Role of alveolar epithelial cell intercellular adhesion molecule-1 in host defense against *Klebsiella pneumoniae*. Am. J. Physiol. 276:L961-L970.

Passariello, C., S. Schippa, C. Conti, P. Russo, F. Poggiali, E. Garaci, and A. T. Palamara. 2006 Rhinoviruses promote internalisation of *Staphylococcus aureus* into non-fully permissive cultured pneumocytes. Microbes Infect. 8:758-766.

Pericone, Christopher D., Overweg, Karin, Hermans, Peter W. M., Weiser, Jeffrey N. (2000). "Inhibitory and Bactericidal Effects of Hydrogen Peroxide Production by *Streptococcus pneumoniae* on Other Inhabitants of the Upper Respiratory Tract". Infect Immun 68 (7): 3990-3997.

Petersen, C. G., T. Ovesen, and C. B. Pedersen. 1998. Acute mastoidectomy in a Danish county from 1977-1996 with focus on the bacteriology. Int. J. Pediatr. Otorhinolaryngol. 45:21-29.

Pietzsch J, Hoppmann S. Human S100A12: a novel key player in inflammation? Amino Acids. 2009 March; 36(3): 381-9.

Qvarnberg Y, Holopainen E, Palua T. Aspiration cytology in acute otitis media. Acta Otolaryngol (Stockh) 1984; 97:443-9.

Revai, K., L. A. Dobbs, S, Nair, J. A. Patel, J. J. Grady, and T. Chonmaitree. 2007. Incidence of acute otitis media and sinusitis complicating upper respiratory tract infection: the effect of age. Pediatrics 119:e1408-e1412.

Rodriguez W J, Schwartz R H. *Streptococcus pneumoniae* causes otitis media with higher fever and more redness of tympanic membranes than *Haemophilus influenzae* or *Moraxella catarrhalis*. Pediatr Infect Dis J 1999; 18:942-4.

Rosenfeld, R. M., and D. Kay. 2003. Natural history of untreated otitis media. Laryngoscope 113:1645-1657.

Rothlein, R., M. L. Dustin, S. D. Marlin, and T. A. Springer. 1986. A human intercellular adhesion molecule (ICAM-1) distinct from LFA-1. J. Immunol. 137:1270-1274.

Rouleau P, Vandal K, Ryckman C, Poubelle P E, Boivin A, Talbot M, Tessier P A (2003) The calcium-binding protein S100A12 induces neutrophil adhesion, migration, and release from bone marrow in mouse at concentrations similar to those found in human inflammatory arthritis. Clin Immunol 107:46-54.

Roy M Vega. Parainfluenza Virus Infections: Differential Diagnoses & Workup. Contributor Information and Disclosures. 2009, Aug. 28.

Rudberg, R. D. 1954. Acute otitis media: comparative therapeutic results of sulphonamide and penicillin administered in various forms. Acta Otolaryngol. (Stockholm) 113 (Suppl.):9-79.

Russo, E., C. W. Smith, E. M. Friedman, E. O, Smith, and S. L. Kaplan. 2004. Cell adhesion molecules and cytokines in middle ear effusions in children with or without recent acute otitis media. Otolaryngol. Head Neck Surg. 130:242-248.

Samuelson, A., S. Borrelli, R. Gustafson, L. Hammarstrom, C. I. Smith, et al. 1995. Characterization of *Haemophilus influenzae* isolates from the respiratory tract of patients with primary antibody deficiencies: evidence for persistent colonizations. Scand. J. Infect. Dis. 27:303-313. VOL. 17,2010 sICAM-1 IN AOM 1915.

Springer, T. A. 1994. Traffic signals for lymphocyte recirculation and leukocyte emigration: the multistep paradigm. Cell 76:301-314.

Sulik, A., M. Wojtkowska, D. Rozkiewicz, and E. Oldak. 2006. Increase in adhesion molecules in cerebrospinal fluid of children with mumps and mumps meningitis. Scand. J. Immunol. 64:420-424.

Teele D W, Klein J O, Chase C, Menyuk P, Rosner B A (1990) Otitis media in infancy and intellectual ability, school achievement, speech, and language at age 7 years. Greater Boston Otitis Media Study Group. J Infect Dis 162:685-694.

Terada, N., A. Konno, T. Yamashita, et al. 1993. Serum level of soluble ICAM-1 in subjects with nasal allergy and ICAM-1 mRNA expression in nasal mucosa. Jpn. J. Allergol. 42:87-93. Uchiyama-Tanaka Y, Mori Y, Kosaki A, Kimura T, Moriishi M, Kawanishi H, Matsubara H (2008) Plasma S100A12 concentrations in peritoneal dialysis patients and subclinical chronic inflammatory disease. Ther Apher Dial 12:28-32.

Vogl T, Propeer C, Hartmann M, Strey A, Strupat K, van den Bos C, Sorg C, Roth J (1999) S100A12 is expressed exclusively by granulocytes and acts independently from MRP8 and MRP14. J Biol Chem 274:25291-25296.

Witkowska, A. M., M. H. Borawska, and M. Gacko. 2006. Relationship among TNF- , sICAM-1, and selenium in presurgical patients with abdominal aortic aneurysms. Biol. Trace Element Res. 114:31-40.

Wittkowski H, Hirono K, Ichida F, Vogl T, Ye F, Yanlin X, Saito K, Uese K, Miyawaki T, Viemann D, Roth J, Foell D (2007) Acute Kawasaki disease is associated with reverse regulation of soluble receptor for advance glycation end products and its proinflammatory ligand S100A12. Arthritis Rheum 56:4174-4181.

Xie, H., and X. X. Gu. 2008. *Moraxella catarrhalis* lipooligosaccharide selectively upregulates ICAM-1 expression on human monocytes and stimulates adjacent naïve monocytes to produce TNF-alpha through cellular crosstalk. Cell. Microbiol. 10:1453-1467.

Yang Z, Tao T, Raftery M J, Youssef P, Di Girolamo N, Geczy C L (2001) Proinflammatory properties of the human S100 protein S100A12. J Leukocyte Biol 69:986-994.

Ye F, Foell D, Hirono K I, Vogl T, Rui C, Yu X, Watanabe S, Watanabe K, Uese K, Hashimoto I, Roth J, Ichida F, Miyawaki T (2004) Neutrophil-derived S100A12 is profoundly upregulated in the early stage of acute Kawasaki disease. Am J. Cardiol. 94:840-844.

We claim:

1. A method of diagnosing and treating bacterial acute otitis media (AOM) comprising:
    (a) measuring the levels of s100A12, Interleukin 10 (IL-10) and Intercellular Adhesion Molecule 1 (ICAM-1) in a sample from a subject;
    (b) comparing the levels of S100A12, IL-10, and ICAM-1 to the respective levels of S100A12, IL-10, and ICAM-1 in a control, wherein the control comprises a sample from an age matched healthy subject;
    (c) diagnosing the subject as having bacterial AOM if the level of one or more of S100A12, IL-10, and ICAM-1 in the sample is greater than the control; and
    (d) administering an antibiotic against bacterial AOM to the diagnosed subject.

2. The method of claim 1, wherein the level of S100A12 is at least 10% greater than the control.

3. The method of claim 1, wherein the sample is a blood sample or serum sample.

4. The method of claim 1, further comprising performing an enzyme-linked immunosorbent assay (ELISA).

5. The method of claim 1, wherein the step of measuring comprises measuring the level of S100A12 mRNA in the sample.

6. The method of claim 1, further comprising performing a hybridization assay, Real-time Polymerase chain reaction (RT-PCR), or Quantitative Polymerase chain reaction (qPCR).

7. The method of claim 1, wherein the subject is a child less than 12 years of age.

8. The method of claim 1, wherein the AOM infection is determined to be a bacterial AOM infection with at least a 50%, 60%, 70%, 80%, 90%, 95%, 97%, or 99% certainty.

9. The method of claim 1, wherein the increased level of S100A12 compared to the control indicates that the acute otitis media (AOM) is caused by *Streptococcus pneumoniae*.

10. The method of claim 1, wherein the increased levels of one or more of s100A12, ICAM-1, and IL-10 compared to the control indicates that the acute otitis media (AOM) is caused by *Streptococcus pneumoniae*.

* * * * *